US008128948B1

(12) United States Patent
Teal et al.

(10) Patent No.: US 8,128,948 B1
(45) Date of Patent: Mar. 6, 2012

(54) COMPOSITIONS AND METHODS FOR ATTRACTING *ANASTREPHA* SPECIES

(75) Inventors: Peter E.A. Teal, Gainsville, FL (US); Spencer S. Walse, Fresno, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 734 days.

(21) Appl. No.: 12/152,570

(22) Filed: May 15, 2008

Related U.S. Application Data

(60) Provisional application No. 60/930,386, filed on May 16, 2007.

(51) Int. Cl.
  *A01N 25/00* (2006.01)
  *A01N 43/04* (2006.01)
(52) U.S. Cl. ............ 424/405; 424/84; 424/406; 514/25; 514/27; 514/53; 514/450; 514/465
(58) Field of Classification Search .................. None
  See application file for complete search history.

(56) References Cited

OTHER PUBLICATIONS

Abstaract of HCAPLUS—# 1994:481684, 121:81684—Epsky et al, in Environmental Entomology (1993), 22(5) 942-7; Food Availability & Pheromone Production by Males of *Anastrepha suspensa* .*
Abstract of CROPU accession # 1988-82930 Mori et al Liebigs Ann. Chem. (1988, # 2, 167-74) Pheromone Synthesis, Synthesis of Lactone Componenets of Pheromone of *Anastrepha suspensa*, Suspenolide & the Enantiomers of *Anastrephin* & *Epianastrephin*.*
Chuman et al 88 in Tetrahedron Lletters, vol. 29, # 50, PPP6561-6564 Suspensolide.*
Gunata, Z. et al., "Enzymatic Synthesis of Monoterpenyl β-D-Glucosides by Various β-glucosidases", Enzyme Microb. Technol., vol. 16, 1994, pp. 1055-1058.
van Rantwijk, F. et al., "Glycosidase-Catalysed Synthesis of Alkyl Glycosides", J. of Molecular Catalysis B: Enzymatic, vol. 6, 1999, pp. 511-532.
Thiem, J., "Applicaitons of Enzymes in Synthetic Carbohydrate Chemistry", FEMS Microbiology Reviews, vol. 16, 1995, pp. 193-211.
Enzymatic Glucosylation of Hydrophobic Alcohols in Organic Medium by the Reverse Hydrolysis Reaction Using Almond-β-Glucosidase, Biotechnology and Bioengineering, vol. 46, 1995, pp. 109-116.
Ponce, W.P. et al., Quantitative Analysis of Pheromone Production in Irradiated Caribbean Fruit Fly Males, *Anastrepha suspensa*, Journal of Chemical Ecology, 1993, 3045-3056, vol. 19, 12.
Nation, J.L., Biology of Pheromone Release by Male Caribbean Fruit Flies, *Anastrepha suspensa*, Journal of Chemical Ecology, 1990, 553-572, vol. 16, 2.

(Continued)

*Primary Examiner* — Neil Levy
(74) *Attorney, Agent, or Firm* — John D. Fado; G. Byron Stover

(57) ABSTRACT

A composition containing suspensolide and optionally at least one of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, or mixtures thereof, and optionally a carrier or carrier material; the composition contains no β-bisabolene and no α-farnesene. A method for attracting *Anastrepha* species (e.g., *A. suspensa*) involving treating an object or area with an *Anastrepha* species attracting effective amount of the above composition.

33 Claims, 26 Drawing Sheets
(2 of 26 Drawing Sheet(s) Filed in Color)

OTHER PUBLICATIONS

Nation, J.L., The Role of Pheromones in the Mating System of *Anastrepha* Fruit Files, 189-205, 1989.

Nation, J.L., The Sex Pheromone Blend of Caribbean Fruit Fly Males: Isolation Biological Activity, and Partial Chemical Characterization, Environmental Entomology, 1989, 27-30, vol. 4, 1.

Nation, J.L., Sex Pheromone Components of *Anastrepha suspensa* and their Role in Mating Behavior, Proceedings of the International Symposium on the Biology and Control of Fruit Flies, 1991, 233-245.

* cited by examiner (a)

(b)

(a)

(b)

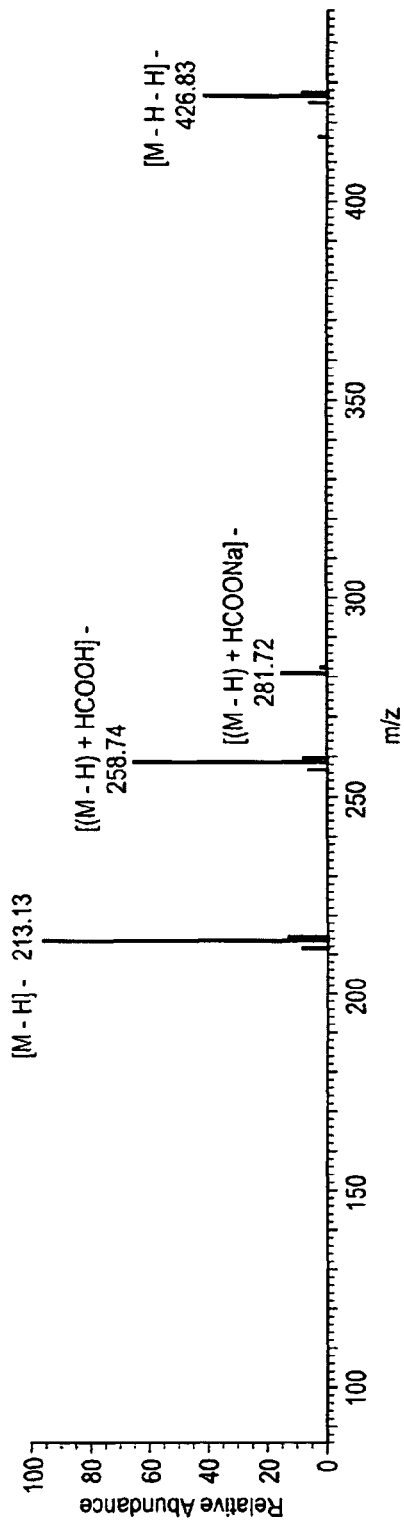
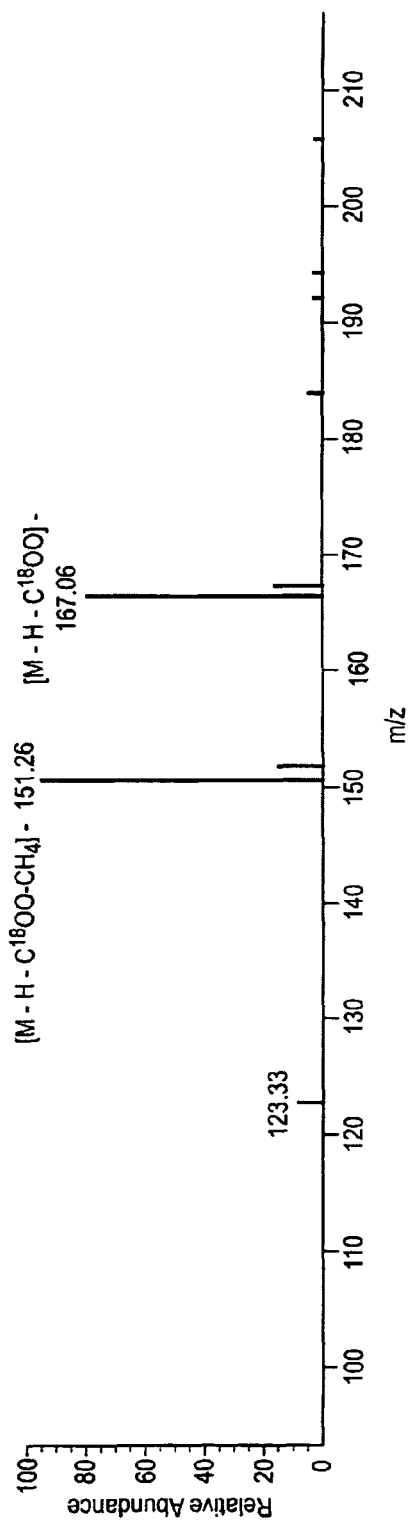
Figure 9A
Figure 9B

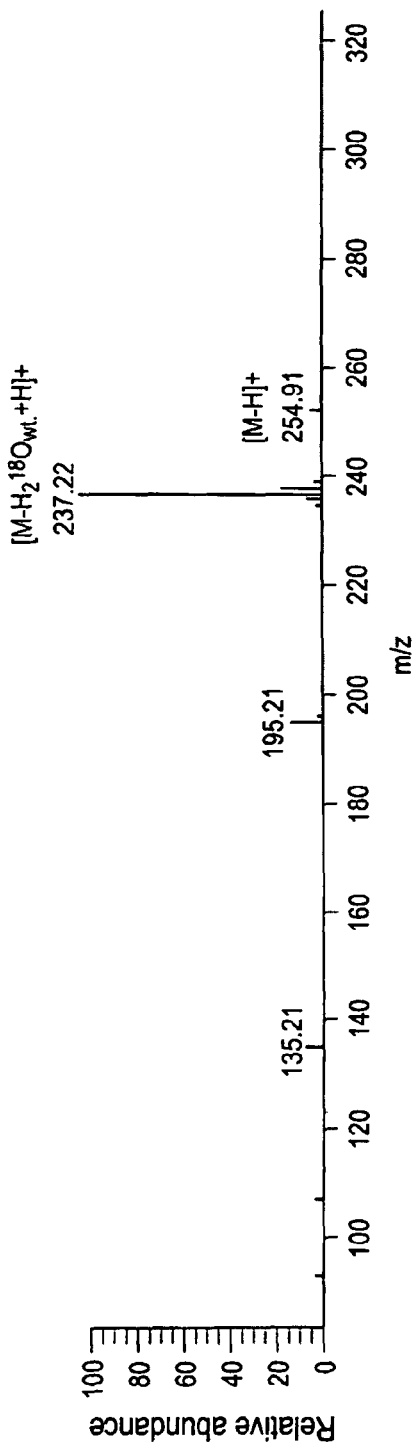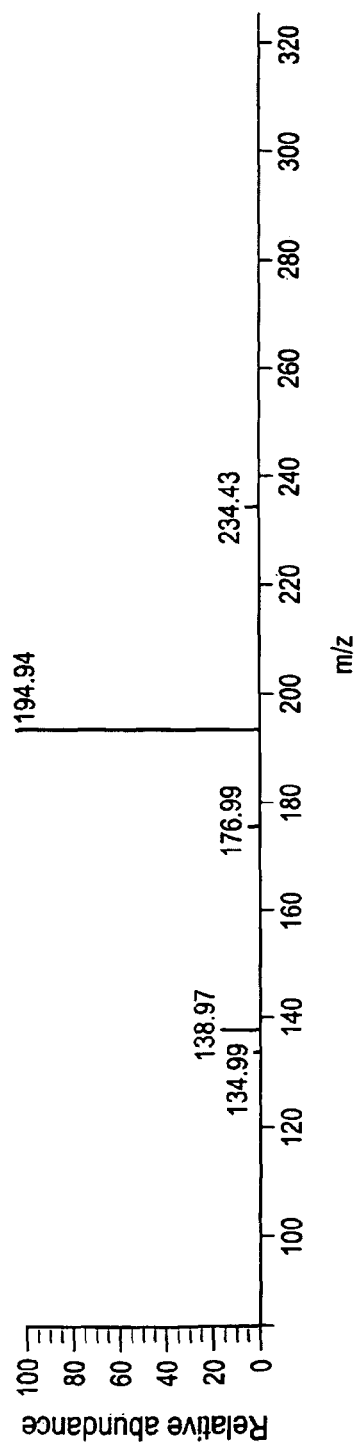
Figure 12A
Figure 12B

COMPOSITIONS AND METHODS FOR ATTRACTING *ANASTREPHA* SPECIES

REFERENCE TO RELATED APPLICATION

This application claims the benefit of U.S. Provisional Application No. 60/930,386, filed 16 May 2007, which is incorporated herein by reference in its entirety.

BACKGROUND OF THE INVENTION

The present invention relates to a composition containing suspensolide and optionally at least one of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetate, or mixtures thereof, and optionally a carrier or carrier material; the composition contains no β-bisabolene and no α-farnesene. The present invention also relates to a method for attracting *Anastrepha* species (e.g., *Anastrepha suspensa*) involving treating an object or area with an *Anastrepha* species attracting effective amount of the composition described herein.

Tephritid flies pose a serious threat to fruit commodities around the world (Landolt, P. J., and R. R. Heath, In: Pest Management in the Subtropics, Integrated Pest Management-A Florida Perspective, pages 197-207, Intercept Ltd, Andover, Hants, UK, 1996). Within the U.S. alone, fruits that can serve as larval hosts had a market value estimated at $7.2 billion in 2002 (USDA-APHIS, Exotic Fruit Fly Strategy Plan (2006), http://www.aphis.usda.gov/ppq/ep/ff/background.htm). Consequently, their populations need to be monitored and controlled. Within Florida and the Greater Antilles, *Anastrepha suspensa* (Diptera: Tephritidae) is a species of concern.

We have developed a composition which slowly releases attractants for insects such as *Anastrepha* species (e.g., *A. suspensa*).

SUMMARY OF THE INVENTION

In accordance with the present invention, there is provided a composition containing suspensolide and optionally at least one of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetate, or mixtures thereof, and optionally a carrier or carrier material; the composition contains no β-bisabolene and no α-farnesene. Also in accordance with the present invention, there is provided a method for attracting *Anastrepha* species (e.g., *A. suspensa*) involving treating an object or area with an *Anastrepha* species (e.g., *A. suspensa*) attracting effective amount of the composition described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

DETAILED DESCRIPTION OF THE INVENTION

Figure 1:
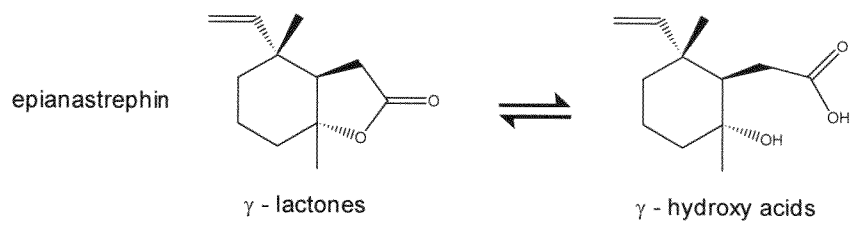
FIG. 1 shows (a) structures of the γ-hydroxy acid precursors and the γ-lactone pheromones, present in the ratio of ~2.5 epianastrephin to anastrephin, within oral secretions deposited by male Caribbean fruit flies and (b) a cross-section schematic of an oral secretion which illustrates the environmentally directed equilibrium that maintains pheromone release over many days (shown here for epianastrephin).
Figure 1:
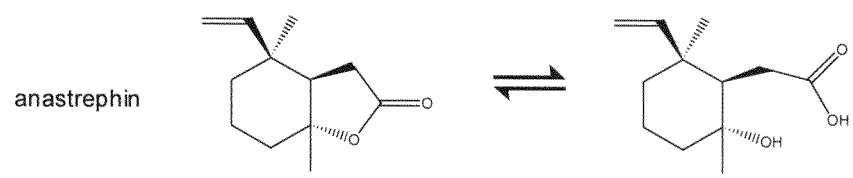
Figure 1:
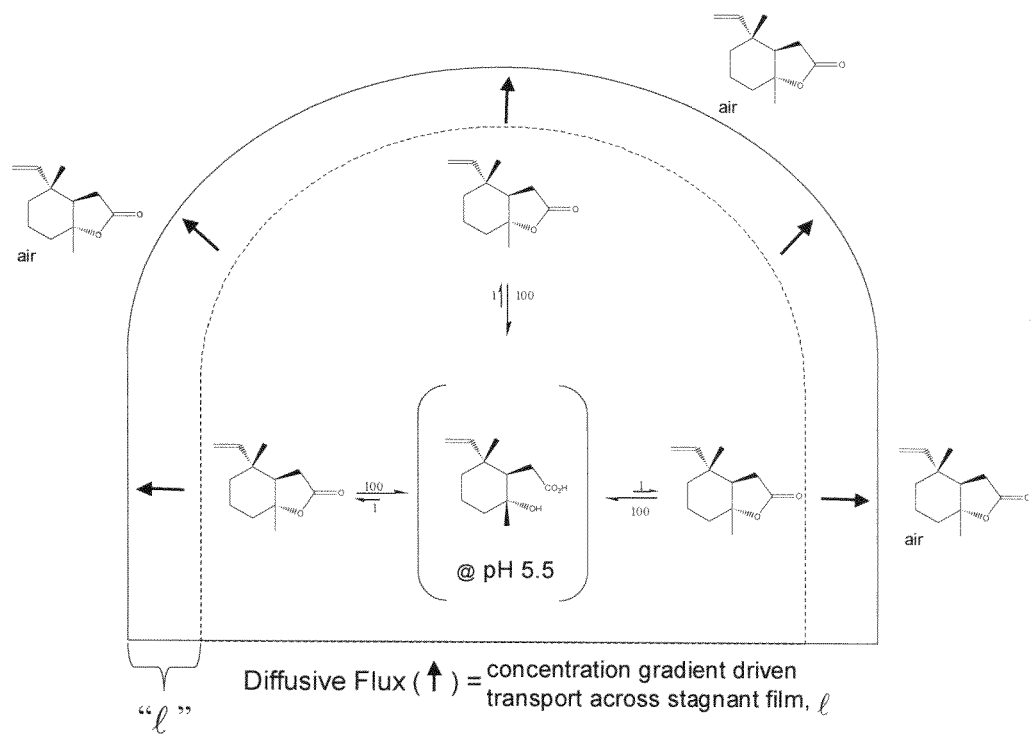

A composition is disclosed for attracting insects (e.g., *Anastrepha* species such as *A. suspensa*), containing suspensolide and optionally at least one of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, or mixtures thereof, and optionally a carrier or carrier material; the composition contains no β-bisabolene and no α-farnesene. Also disclosed is a method for attracting *Anastrepha* species (e.g., *A. suspensa*) involving treating an object or area with an *Anastrepha* species attracting effective amount of the composition described herein.

The attractant composition of the present invention may be applied with a carrier component or carrier (e.g., biologically or agronomically acceptable carrier). The carrier component can be a liquid (e.g., water, sugar solution) or a solid material. As is known in the art, the vehicle or carrier to be used refers to a substrate such as a membrane, hollow fiber, microcapsule, cigarette filter, gel, polymers, septa, or the like. All of these substrates have been used to release insect attractants in general and are well known in the art. Suitable carriers are well-known in the art and are selected in accordance with the ultimate application of interest. Data presented herein indicated that sugar solutions were an effective carrier; however, solid carriers such as clays, cellulose-based and rubber materials and synthetic polymers can also be used. The sugar solution generally contains fructose and/or sucrose and optionally other sugars such as glucose; for example, ~D-glucose: 2 D-fructose: sucrose ratio.

The amount of attractant used will be at least an effective amount. The term "effective amount," as used herein, means the minimum amount of attractant needed to attract the insects (e.g., *Anastrepha* species such as *A. suspsensa*) to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would be statistically significant in comparison to a negative control. The attractant composition may or may not contain a control agent for insects, such as a biological control agent or an insecticide known in the art to kill insects. Other compounds (e.g., insect attractants known in the art) may be added to the attractant composition provided they do not substantially interfere with the intended activity of the attractant composition; whether or not a compound interferes with attractant activity, can be determined, for example, by the procedures utilized below.

A method is disclosed for attracting insects (e.g., *Anastrepha suspensa* flies) to an object (e.g., insect trap) or area involving treating (or exposing) the object or area with the above composition (optionally including the carrier material or carrier). The method may be used to attract *Anastrepha* species such as *A. suspensa, A. ludens* (Mexican fruit fly), *A. obliqua* (West Indian fruit fly), and *A. fraterculus* (South American fruit fly). The *Anastrepha* species which can be attracted can easily be determined by one skilled in the art given the teaching of this application. For example, one skilled in the art could follow the procedures utilized below; the attraction would be statistically significant in comparison to a negative control.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Chemicals: Standards (>99%) of enantiomerically pure epianastrephin and anastrephin were donated by R. R. Heath (USDA-ARS, Miami, Fla.). Their corresponding γ-hydroxy acids were synthesized using a method for opening the rings of terpenoid lactones as described by Harwood and Moody (Harwood, L. M., and C. J. Moody, Experimental Organic Chemistry: Principles and Practice, Blackwell Scientific Publications, Oxford, UK, 1989). All other chemicals were obtained from commercial sources. Stock solutions were prepared routinely with Barnstead E-pure™ water (18 MΩ-cm) or acetonitrile (HPLC grade, >99.9%) and stored at 4° C.

Gas Chromatography-Mass Spectrometry: A modified method of Heath et al. (Heath, R. R., et al., J. Chem. Ecol., 19: 2395-2410 (1993)) was used with a Varian 3400 gas chromatograph and a Finnigan MAT Magnum™ ion trap mass spectrometer (GC-ITMS) operated with 70 eV electron impact (EI) ionization (11765 mV filament bias) or isobutane chemical ionization (CI). Full scan spectra were acquired over the ranges m/z 70 to 400 at 0.85 s per scan. Cool on-column injections (1 μL) were at 40° C. with a constant 260° C. detector and He carrier gas (1.4 mL/min). The transfer-line and manifold temperatures were 240° C. and 220° C., respectively. GlasSeal connectors (Supelco®) fused three columns in series; a primary deactivated column (L=8 cm, ID=0.53 mm), a HP-1MS retention gap column (L=2 m, ID=0.25 mm, df=0.25 μm), and a J&W DB-1 analytical column (L=30 m, ID=0.25 mm, df=0.25 μm). The oven program was isothermal at 40° C. for 5 min, heated at 11° C./min to 200° C., isothermal for 10 min, heated at 25° C./min to 250° C., and then isothermal for 15 min. Retention times and fragmentation patterns of purchased or synthesized standards were compared with natural products. Method detection limits in EI m/z 195 select ion mode were as follows: epianastrephin, $3.4 \times 10^{-9}$ M; anastrephin; $3.3 \times 10^{-9}$ M. GC-EIMS of epianastrephin and anastrephin, m/z (% relative intensity) 195 ($M^+$+1, 3), 179 (4), 166 (3.5), 151 (3.5), 135 (10), 124 (7), 108 (17), 93 (23), 79 (30).

High Pressure Liquid Chromatography-Mass Spectrometry (MS): A Thermo Separation Products Spectra SYSTEM P4000 pump, ThermoFinnigan UV6000LP LDC photodiode array detector (PDA), and Finnigan LCQ DecaXP Max mass spectrometer (HPLC-MS) were used. Mass spectra were obtained using electrospray ionization (+/−ESI) with 5 kV spray voltage and 275° C. capillary temperature. Sheath and sweep gas flow rates (arb) were 40 and 20, respectively. Flow through the column (1 ml/min) was split 10:1 between the PDA and MS; eluants were (a) 0.1% formic acid in ACN (acetonitrile), (b) 10 mM ammonium formate, and (c) 10 mM ammonium formate in 90% ACN. An YMC-Pack ODS-AQ analytical column (L=250 mm, ID=4.6 mm, S=5 μm, 20 nm) was used with the following elution program: isocratic (4a: 72b:24c) for 13.5 min, to 4:0:96 over 4.5 min, isocratic (4:0:96) for 17 min. Retention times of synthetic standards are presented in Table 1 and were used to verify products. The standard deviation associated with triplicate injections was used to assess error in all HPLC concentration measurements. Method detection limits for (+)ESI m/z 195 SIM were as follows: epianastrephin, 40 ng; anastrephin, 42 ng; epianastrephin hydroxyl acid, 10 ng; anastrephin hydroxyl acid, 11 ng.

Insects and Collection of Oral Secretions: Caribbean fruit flies were cultured as described previously (Teal, P. E. A., and F. Lu, Arch. Insect Biochem. Physiol., 48: 144-154 (2001)) and OS from 11-14 day old adults was harvested and collected using glass capillary (1 mm i.d.) that penetrated the Teflon® septum of a vial held under slight negative pressure at 4° C. Collections were made 2±0.5 h prior to sunset, pooled until ~0.6 mL was accumulated, and stored at −70° C.

Pheromone Speciation in oral secretions: Oral secretions (0.5 mL) were added to a 5-mL Pyrex® Kurderna Danish tubes and diluted to 1 mL. The samples were transferred to Supelco® DSC-18 1-mL solid phase extraction cartridges and flushed into 2 mL conical tubes. After rinsing the DSC-18 tubes with water (3×1 mL), the analytes were eluted with (3×1 mL) 0.05% formic acid in 50% ACN. Eluant fractions (3×1 mL) were concentrated to 0.5 mL and 2 μL ACN+360 μg of sclareolide (Sigma) as a standard was introduced prior to analysis via HPLC-ESIMS.

Epianastrephin and anastrephin were recovered from oral secretions by diluting the samples to 1 mL by addition of water and then adding 1 ml of hexane containing 800 ng of teradecane (internal standard) prior to vortexing for 2 min. Emulsions were broken by the addition of ~100 mg NaCl and the hexane extract removed for analysis by GC-ITMS.

Flight Tunnel Bioassays and Volatile Collections: All "dual-choice" bioassays were conducted in Plexiglas® flight tunnels (150×30×30 cm) housed within a greenhouse, as described by Heath et al. (Heath, R. R., et al., Fla. Entomol., 76: 233-244 (1993)). Ambient air supply, originating from a source external to the greenhouse, was charcoal-filtered. Air flow, metered to 660 $cm^3$/min, was directed through glass chambers and into the tunnel through the insect isolation traps lined with sticky paper and capped with orange-colored plastic snap cap lids having a 1.1 cm diameter hole in the center to accommodate entry by the flies. The traps were positioned symmetrically at mid height, 5.1 cm to the left and right of the tunnel midline and 5 cm from the upwind end. Four such flight tunnel assays were utilized and positions of traps within each (left or right) were swapped before each use.

Flies were presented a choice between volatiles released from male oral secretions or female oral secretions (blank). Other tests compared blanks to female oral secretions spiked with amounts of synthetic γ-hydroxy acids of epianastrephin (17 ng) and anastrephin (7 ng) equivalent to that naturally present in 10 μl of male oral secretions. We also directly compared spiked female oral secretions to male oral secretions and male oral secretions to volatiles released by five caged males. Five sexually mature (12-14 day old) flies were released into the tunnels between 22:00 and 23:00 h. Glass slides, onto which 10 μl of oral secretion substrate had been deposited 24 h earlier, were inserted into the glass chambers at 04:00 h. The number of flies in traps was counted hourly between 5:00-21:00 h. All flies, captured or not, were removed a day after their release and the flight tunnels were wiped clean with 1:1 methanol/water in preparation for the next assay.

Volatile collections were conducted in the greenhouse using glass chambers and an ambient air supply identical to those used for bioassays. Samples, consisting of ten 10 μL aliquots of male oral secretions or female oral secretions spiked with the γ-hydroxy acids were placed on glass slides and positioned in the glass chambers at 9:00 h along with a digital thermo-hygrometer. Filters for collection of volatiles, containing 20 mg of Super-Q adsorbent (Altech®), were attached to the outports of the chambers. Collection filters were changed and temperature and humidity were recorded at the same time as flies were counted in flight tunnel bioassays. Chemicals were eluted from volatile collection filters by flushing them with 3 ml of methyl tert-butyl ether (MTBE) into 10 mL Pyrex® Kurderna Danishes containing 0.5 mL MTBE+400 ng of tetradecane. The eluant was then reduced to 0.5 mL with a gentle $N_2$ gas stream and used for quantitative and qualitative chemical analyses via gas chromatography-mass spectrometry. Collection efficiencies of synthetic pheromone standards applied to the filters were >98%.

Results and discussion: Lek mating strategies, where males aggregate in display areas to attract, court and mate with females, have evolved in many insects such as flies, and especially tropical species of Tephritid fruit flies, which employ this mating strategy (Shelly, T. E., and T. S. Whittier, The evolution of mating systems in insects and Arachnids, eds. B. Crespi and J. C. Choe, Cambridge Press, Cambridge, UK, 1997; Sivinski, J. M., and T. Burk, In: Fruit Flies Their biology, natural enemies, and control, eds. A. S. Robinson and G. Hooper, pages 343-350, Elsevier, 1989). Interestingly, lek sites are commonly frequented day after day despite the presence of nearby alternate sites which appear as good as the chosen site (Sivinski, J., J. Insect Behav., 2: 3-13 (1989); Nation, J. L., J. Chem. Ecol., 16: 553-572 (1990)). Fruit flies mark lek sites with oral and anal secretions (Nation, J. L., J. Chem. Ecol., 16: 553-572 (1990); Sivinski, J. M., et al., J. Insect Behav., 7: 43-51 (1994); Teal, P. E. A., and F. Lu, Arch. Insect Biochem. Physiol., 48: 144-154 (2001)). Oral secretions constitute the largest pool of marking substrate (c.a. 0.5-1 µL/male/day).

The fact that relatively little pheromone seemed to be deposited at lek sites and that these sites remain attractive for many days was initially an enigma. Additionally, collection of volatiles released from oral secretions over a 72 h period yielded nine-fold more pheromone than was extractable in organic solvents, and heating oral secretions to 90° C. resulted in our being able to extract at least three times as much pheromone as was present in samples extracted at 25° C. Interpreted individually, these findings provided little insight into the mechanism of prolonged pheromone release. However, collectively they led to our hypothesis that surprisingly anastrephin and epianastrephin, neither of which is very soluble in water (~40 mg/L; EPI-Suite; WATERNT v1.00, U.S. E.P.A., 2002), were somehow incorporated into the aqueous matrix of the oral secretion and released slowly. We reasoned that if this were so, more polar forms of the pheromones should exist. Using reverse phase liquid chromatography, we recovered fractions having the same retention volumes as anastrephin and epianastrephin, as well as much more polar fractions which, when heated, surprisingly contained 2-3 times the amount of anastrephin and epianastrephin. Liquid chromatography-mass spectrometry of the oral secretions confirmed our suspicions because water soluble γ-hydroxy acid analogues of anastrephin and epianastrephin (FIG. 1) were surprisingly present in the same ratio as the γ-lactones but at twice the concentration.

Figure 2:
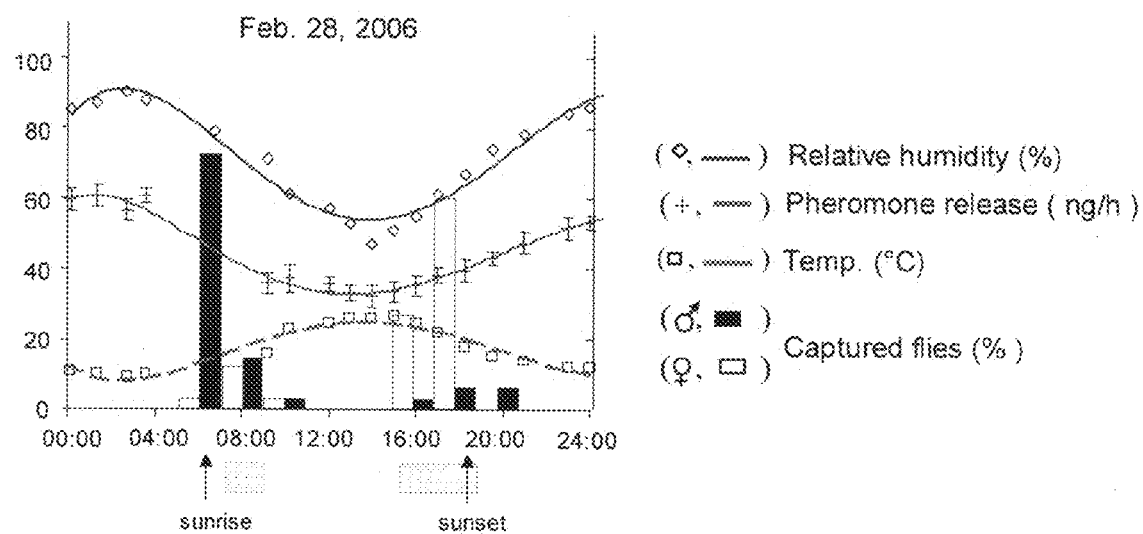
FIG. 2 shows hourly variation of temperature, humidity, and pheromone release ($\bar{x}\pm s$, n=3) from male oral secretions (10 μL) relative to temporal capture of flies over the preceding week in "dual-choice" flight tunnel bioassays. Cumulative data from attraction to female oral secretions spiked with the γ-hydroxy acids versus equivalent amounts of male oral secretion is shown and was obtained from 8 replicates of five-fly tests with overall trap capture efficiencies of 36/40 for males and 35/40 for females. Most male attraction occurred after the maximum in pheromone release and just prior to the morning episode of biological activity (▬).

We synthesized the γ-hydroxy acid analogues, dissolved them in water (solubility ~4600 mg/L; EPI-Suite; WATERNT v1.00, U.S. E.P.A., 2002)), and recovered the closed ring lactone pheromones, anastrephin and epianastrephin, in both volatile collections from acids in the water mixture and from organic extracts. This led to our conclusion that there were, in fact, naturally produced precursors of the lactone pheromones. To gain better insight into the acid to lactone conversion and its relation to pheromone emission, the equilibrium and kinetics of their aqueous speciation and liquid to air partitioning (i.e., Henry's Law) were investigated under controlled conditions. Our results indicated that pheromone release from the oral secretions occurred with a diffusion-limited rate that could be described by a stagnant boundary model under liquid-film control (FIG. 1(b)) (Crank, J., The mathematics of Diffusion, Oxford University Press, London, 1975; Carslaw, H. S., and J. C. Jaeger, Conduction of heat in Solids, Oxford University Press, London, 1959). Experimental data showed that depositing the acids at lek sites surprisingly extended emission of the lactone pheromone components by ~100 fold over what would be expected if only the lactones were deposited. Data also showed that sugar-based oral secretions function as a humectant; its viscosity, and thus diffusion-limited release of pheromone, varied markedly with relative humidity. The kinetic model was tested under natural conditions and the results showed that the release of anastrephin and epianastrephin from oral secretions exhibited a periodicity coincident with diel changes in relative humidity (inversely related to temperature) (FIG. 2).

Figure 3:
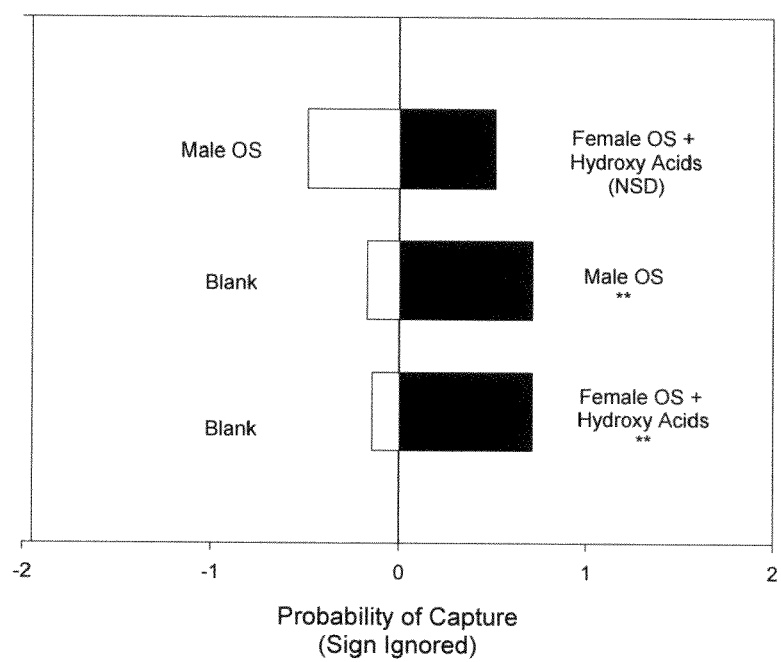
FIG. 3 shows results of dual choice flight tunnel tests in which males were provided a choice of flying to volatiles released from 10 μl of female oral secretion (OS) (control) or natural male OS or female OS spiked with the appropriate amounts (2.4 ng/μl) of the γ-hydroxy acid analogues of anastrephin or epianastrephin in the naturally occurring 1:2.5 ratio. Five males released per replicate with each replicate repeated 8 times. Data were analyzed using paired t-test and the means converted to probabilities of capture for graphics. Statistical values for female oral secretion+γ-hydroxy acid analogues vs. blank: t=8.4, 7df, P=0.0; male oral secretion vs. blank: t=6.1, 7df, P=0.001; and for male oral secretion vs. female oral secretion+γ-hydroxy acid analogues; t=0.0, 7df, P=1.0. Asterisks denote "choices" that resulted in significantly different capture (α=0.05).

The identification of the γ-hydroxy acid analogues in oral secretion markings, and knowledge that they were converted to anastrephin and epianastrephin abiotically, pointed strongly to a function in the natural production of aggregation and/or sexual pheromones. Flight tunnel studies demonstrated that neither males nor females were attracted to volatiles from female oral secretions as they do not contain any pheromone components or the γ-hydroxy acid analogues. We reasoned that if the conversion of the acids to anastrephin and epianastrephin were responsible for the attraction of flies to lek sites then we should be able to fortify female secretions with the γ-hydroxy acid analogues, produce the lactone pheromones, and attract flies to these "artificial" markings. This is exactly what happened as both males and females were surprisingly attracted equally to equivalent amounts of oral secretions from males and oral secretions from females spiked with the γ-hydroxy acids (FIG. 3).

An interesting feature of these assays was that the attraction of the individual sexes to oral secretions was synchronized around the different periods of activity that occur each day: at dawn and ~3 h prior to dusk. The majority of females (ca. 90%) were captured in the afternoon, when mating occurs, as would be expected if the compounds acted as sex pheromones. However, this was in the absence of naturally produced male sex pheromone. Without being bound by theory, we believe that abiotic release of epianastrephin and anastrephin from previously deposited oral secretions had little effect on female attraction in nature for two reasons. First, the contribution of pheromone from oral secretions (100 µL) during the afternoon mating period (ca. 35 ng/hr, FIG. 2) is exceedingly small compared to the amount released by males (~1 µg/h). Second, when given a choice between volatiles from five males or 10 µL it of artificially deposited male oral secretions, females always chose the males during the reproductive period (p=0.87±0.005, n=8; t=8.2). Thus, abiotic release of pheromone from oral secretions appeared to be masked during the afternoon mating period. In contrast, essentially all males were attracted at or just after dawn, a period when biotic release of pheromone was low or nonexistent and when relative humidity and abiotic release of pheromone from oral secretions was high (FIG. 2). As such, our data surprisingly showed that lek sites were most chemically obvious to males just prior to and at dawn when anastrephin and epianastrephin emission resulted almost exclusively from abiotic release. It was not until later in the day that males began to engage in a variety of behaviors, including pheromone release, to demarcate territories and fight to establish their rank within the lek.

Unlike monophagous tephritid species that mate on and guard host fruit, polyphagous, lek forming tephritids mate on the undersides of leaves that are not exclusively associated with fruit that serve as oviposition resources. These lek mating systems probably evolved along with the development of polyphagy with the move from signaling on host fruit to the undersides of leaves evolving as a way to reduce predation. Although the cryptic nature of the lek sites may be an effective way to reduce predation, it also minimizes the ability of flies to find lek sites visually. In the absence of visual cues, the flies developed the abiotically regulated slow release chemical signaling system we have documented. This system which emits chemical attractants for many days allows flies to establish an essentially permanent signaling sites for communal aggregation and mating.

Example 2

Chemicals: Standards (>99%) of enantiomerically pure epianastrephin and anastrephin as well as (3E,8E)-suspensolide were purchased from Nitto Denko Corp. (Lot #890106). Their corresponding hydroxy acids (γ or Ω) were synthesized as above; Barnstead E-pure™ water (18 MΩ-cm) or Isotec™ $^{18}$O-water (95 atom %) (1 mL), adjusted to pH≧14 with 5 mg NaOH, was added drop-wise with rapid stirring over 20 min to a solution of 10 mg purified substrate (0.05 mmol) in 0.5 mL anhydrous isopropanol at 35° C. Reaction progress was monitored, and products separated, via (+) ESI HPLC-MS. The γ-hydroxy acids of epianastrephin and anastrephin were cyclized by the acidification of aqueous solutions at 50° C. to pH 3. Hexane-extractable γ-lactones were removed after three hours, dried with anhydrous $MgSO_4$, and concentrated. The cyclization of 10-hydroxy-4,8-dimethyldeca-3(E), 8(E)-dienoic acid to suspensolide followed the protocol of Vecchio, G., and A. C. Oehschlager (J. Org. Chem., 59: 4853-4857 (1994)). All other chemicals were obtained from commercial sources unless otherwise noted.

Figure 4:
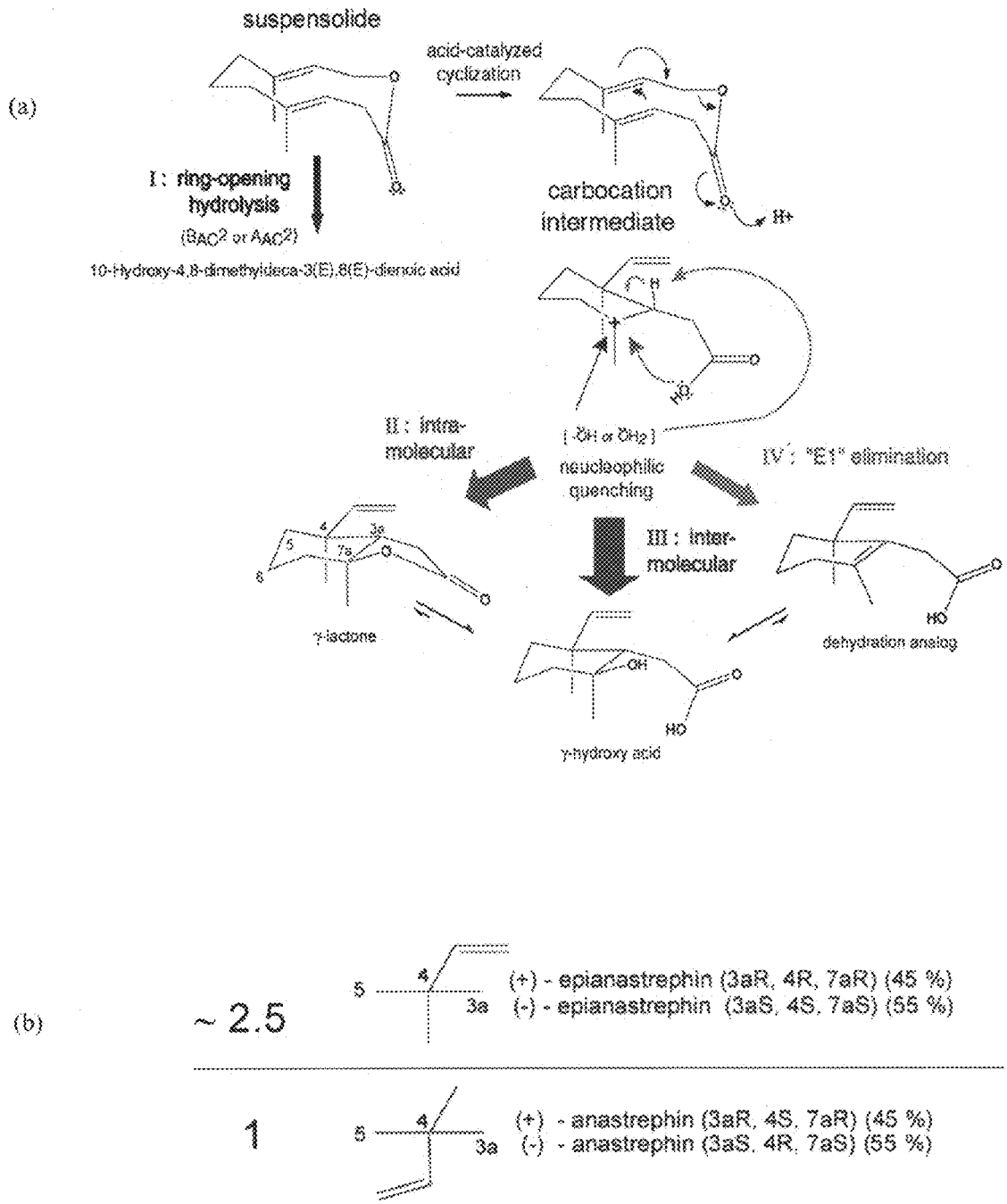
FIG. 4 shows: (a) proposed mechanism of suspensolide hydrolysis and corresponding product manifold. Over pH 5-6 and 25° C., the product distribution III>II>>IV>>>I, occurred rapidly (<2 min) and was consistent with that recovered within fresh oral secretions (pH 5.7) that males deposit at mating sites. Under these conditions, the aqueous interconversion of major products was relatively slow. (b) Fischer projections illustrating a diastereomeric relationship between the pheromones. A ~2.5 epianastrephin to anastrephin product ratio was observed for pathways II and III; in both cases, nucleophilic attack was apparently regioselective as 7a-epimer "cis-fused" equivalents were detected at only trace levels (<5%).

(6R and 6S)-2,6-dimethyl-6-vinyl-cyclohexeneacetic acid (dehydration) analogs: γ-hydroxy acids of (−) anastrephin and (+) anastrephin were used to synthesize the 6R and 6S dehydration analogs, respectively. Methyl esterification ($CH_2N_2$), triphenylphosphine-iodine tertiary alcohol dehydration (Alvarez-Manzaneda, E. J., et al., Tetrahedron Lett., 45: 4453-4455 (2004)), and hydrolysis under mild basic conditions ($K_2CO_3$ aq. in methanol, 15° C.) yielded the analogs in >90% yield. Attempts with (+) epianastrephin and (−) epianastrephin to synthesize the 6R and 6S dehydration analogs, respectively, were far less successful (<5% yield); molecular models suggested steric effects from the vinyl moiety hindered methine proton abstraction. Accordingly, the synchronicity between the development of C4 stereochemistry and the incidence of pathway IV (FIG. 4) is curious.

2,6-dimethyl-6-vinyl-cyclohexeneacetic acid: $^1$H NMR (600 mHz, methanol-$d_4$) δ: 1.12 (s, C6-Me), 1.46-1.54 (m, C5-$H_A$+$H_B$), 1.54-1.65 (m, C4-$H_A$+$H_B$), 1.66 (s, C2-Me), 1.98-2.12 (m, C3-$H_A$+$H_B$), 3.07 (d, $^2$J=17.7 Hz, αC1-$H_A$), 3.18 (d, $^2$J=17.7 Hz, αC1-$H_B$), 4.91 (dd, $^2J_{gem}$=1.6, $^3J_{trans}$ 17.5, βC6-$H_{trans}$), 5.04 (dd, $^2J_{gem}$=1.6, $^3J_{cis}$ 10.6, βC6-$H_{cis}$), 5.71 (dd, $^3J_{cis}$ 10.6, $^3J_{trans}$ 17.5, αC6-H). HMQC and HMBC $^{13}$C NMR (600 mHz, methanol-$d_4$) δ: 18.5 (C4), 19.5 (C2-Me), 23.7 (C6-Me), 32.1 (C3), 34.8 (αC1), 37.5 (C5), 41.9 (C6), 112.0 (βC6), 127.0 (C1), 134.5 (C2), 146.4 (αC6), 172.2 (βC1). GC-CIMS of methyl ester, m/z (% relative intensity) 209 ($M^+$+1, 85), 195 (2), 177 (7), 135 (6):

Gas Chromatography-Mass Spectrometry: A modified method of Heath et al. (Heath, R. R., et al., J. Chem. Ecol., 19: 2395-2410 (1993)) was used with a Varian 3400 gas chromatograph and a Finnigan MAT Magnum™ ion trap mass spectrometer (GC-ITMS) operated with 70 eV electron impact (EI) ionization (11765 mV filament bias) or isobutane chemical ionization (CI). Full scan spectra were acquired over the ranges m/z 40 to 400 at 0.85 s per scan. Cool on-column injections (1 µL) were at 40° C. with a constant 260° C. detector and He carrier gas (1.4 mL/min). The transfer-line and manifold temperatures were 240° C. and 220° C., respectively. GlasSeal connectors (Supleco®) fused three columns in series; a primary deactivated column (L=8 cm, ID=0.53 mm), a HP-1MS retention gap column (L=2 m, ID=0.25 mm, df=0.25 µm), and a J&W DB-1 analytical column (L=30 m, ID=0.25 mm, df=0.25 µm). The oven program was isothermal at 40° C. for 5 min, heated at 11° C./min to 200° C., isothermal for 10 min, heated at 25° C./min to 250° C., and then isothermal for 15 min.

High Pressure. Liquid Chromatography-Mass Spectrometry: A Thermo Separation Products Spectra SYSTEM P4000 pump, ThermoFinnigan UV6000LP LDC photodiode array detector (PDA), and Finnigan LCQ DecaXP Max mass spectrometer (HPLC-MS) were used. Mass spectra were obtained using electro-spray ionization (+/−ESI) with 5 kV spray voltage and 275° C. capillary temperature. Sheath and sweep gas flow rates (arb) were 40 and 20, respectively, and the mobile phase flow rate was 1 ml/min. After passing through the PDA, the eluant was split; ~10% was directed to the MS and the remainder collected. Mobile phase composition was (a) 0.1% formic acid in CAN, (b) 10 mM ammonium formate, and (c) 10 mM ammonium formate in 90% ACN. An YMC-Pack ODS-AQ analytical column (L=250 mm, ID=4.6 mm, S=5 µm, 20 nm) was used with the following elution program: isocratic (4a:72b:24c) for 13.5 min, to 4:0:96 over 4.5 min, isocratic (4:0:96) for 17 min.

Batch hydrolyses: A series of 0.01M buffers were adjusted with varying amounts of NaCl to ionic strengths of u=0.1 M. Solution pH was monitored before and after experiments; it was adjusted by the drop-wise addition of 0.01M HCl and NaOH to 3 ($H_3PO_4$), 5.5 ($NaHCO_3$), 8 ($NaH_2PO_4$), or 10 ($Na_2CO_3$).

Buffers at 25° C. were transferred (1 mL) to 9-mm amber crimp-top (Teflon®-sealed) 2-mL GC vials. Suspensolide in anhydrous acetonitrile or methanol (50 µL) was added to afford initial aqueous concentrations of 0.9 mM and the solution was rapidly mixed for 10 s on a vortex Genie® mixer. Aqueous samples (10 µL) were removed with a 25-µL syringe and combined with 2 µL ACN containing 6 µg (+)-sclareolide as an external standard for HPLC.

GC was used to quantify lactones at the conclusion of each experiment. Hexane (1 mL), containing 0.8 mL of tetradecane as an internal standard, was added to the vials and extractable analytes were removed from the water by rapidly mixing for 2 min on a vortex Genie® mixer. Emulsions were broken with NaCl, after which the hexane layer was transferred to vials for analysis by GC. The remaining solution was concentrated to dryness via Speed Vac® and dissolved in a methanolic solution of diazomethane. Extraction with pentane and subsequently $H_2O$ (0.5 mL each) yielded methyl esters amenable to GC within the organic phase. Initial suspensolide concentrations were measured (quadruplicate) via analogous introduction into 1 mL hexane+internal standard.

The details regarding the aqueous equilibrium distribution between the acid and the lactone forms of epianastrephin and anastrephin (~100 acid:1 lactone), as well as the kinetics of associated inter-conversion, which is slow relative to suspensolide hydrolysis, were reported above. Only trace levels (<2%) of the dehydration analog were detected in these experiments.

When the dehydration analog was hydrolyzed over a 3 day time course at pH 5.5 and 35° C., a ~15% loss of the suspensolide was observed with the following distribution of products (rel. % of loss; $\bar{x}\pm s$; n=6): anastrephin γ-hydroxy acid (38.6±5.1%), anastrephin (17.3±4.2%), "cis-fused" anastrephin (5.8±4.2%), epianastrephin γ-hydroxy acid (3.6±2.3%), epianastrephin (1.7±1.2%), "cis-fused" epianastrephin (1.1±0.5%).

Pheromone distribution within insects: Pheromone collections, from an established culture of Caribbean Fruit Flies, were made 1±0.5 h prior to sunset during peak production. The salivary glands and crops of ten mature males were excised as previously described (Teal, P. E. A., and F. Lu, Arch. Insect Biochem. Physiol., 48: 144-154 (2001)), less the use of physiological saline. The oral secretions from ten other males were harvested with a glass capillary (1 mm i.d.) that penetrated the Telfon® septum of a vial that was under slight negative pressure at 4° C.

The salivary glands, crops, and oral secretions were pooled into separate BioRAD 2-mL EZ micro tubes and 1 mL hexane, containing 0.8 nL of tetradecane as an internal standard was added to each. The samples were processed and analyzed with GC as described above. Aqueous residues from the crops and oral secretions were then diluted to 1 mL. The sample was transferred to Supelco® DSC-18 1-mL solid phase extraction cartridges. After rinsing the cartridges with water (3×1 mL), the analytes were desorbed with (3×1 mL) 0.05% formic acid in 50% ACN and collected in micro tubes. Eluants were combined and dried via Speed Vac®. Samples were processed and analyzed as described in the aqueous product work-up of suspensolide hydrolyses.

The sugar loading and composition in freshly collected OS was determined (Hendrix, D. L., Crop Science, 33: 1306-1311 (1993)) to be 33.2±2.1 wt. % in solution at a ~D-glucose: 2 D-fructose: sucrose ratio. The grand mean percentages (±SE, n=18; Skoog, D., and J. Leary, Principles of Instrumental Analysis, Fourth Edition, Saunders College Publ., Fort Worth, Tex. (1992)) of lactone and acid forms of epianastrephin and anastrephin in samples were 28±7% and 61±6% respectively, and accounted for ~35±5 ng/μL. The ratio of epianastrephin to anastrephin, ~2.5:1, was consistent between both the acid and lactone forms. The dehydration analogs accounted for 11±4% of the potential ES/AS signal, ~50% of which are present as diastereomeric glycosyl ester conjugates having MW 401 ((6R) and (6S) β-D-glucopyranosyl 2,6-dimethyl-6-vinyl-cyclohex-1-ene-1-acetoate) (Walse, S. S., et al., J. Nat. Prod., in press (2008)). None of these pheromone components were detected in female OS.

Flight Tunnel Bioassays and Volatile Collections: All "dual-choice" bioassays were conducted in Plexiglas® flight tunnels (150×30×30 cm), housed within a greenhouse, as described by Health et al. (Heath, R. R., et al., J. Chem. Ecol., 19: 2395-2410 (1993)). Ambient air supply, originating from a source external to the greenhouse, was carbon-filtered. An additional air flow, metered to 660 cm$^3$/min, was directed through glass chambers and into the tunnel through insect isolation traps that were positioned symmetrically at midheight 5 cm from the upwind end and 5.1 cm to the left and right of the tunnel center. Four such flight tunnels were utilized and positions of traps within each (left or right) were swapped before each use.

Figure 7:
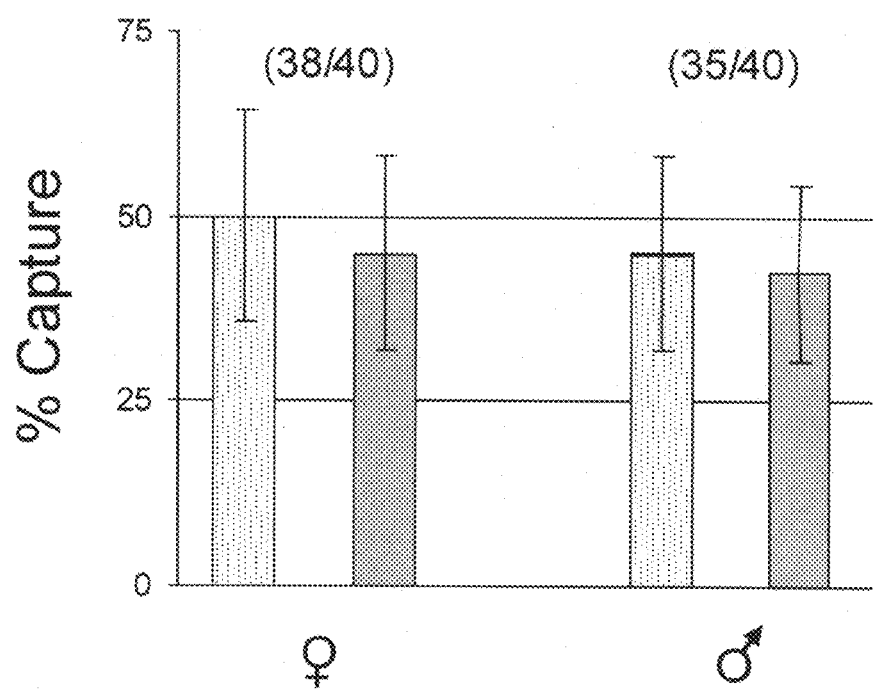
FIG. 7 shows results of dual-choice flight tunnel tests, developed by Heath et al. (Heath, R. R., et al., J. Chem. Ecol., 19: 2395-2410 (1993)), in which flies could discriminate between ~equal amounts of volatile pheromones emanating from 10 μl of synthetic sugar solutions seeded with suspensolide (☐) or natural male oral secretions (■). Five male or female flies were released per replicate (n=8, $\bar{x}\pm s$) with total capture of each sex listed in parenthesis. Data were analyzed using paired t-test: female response; t=0.5, 7df, P=0.6, and male response; t=0.3, 7df, P=0.8.
Figure 8:
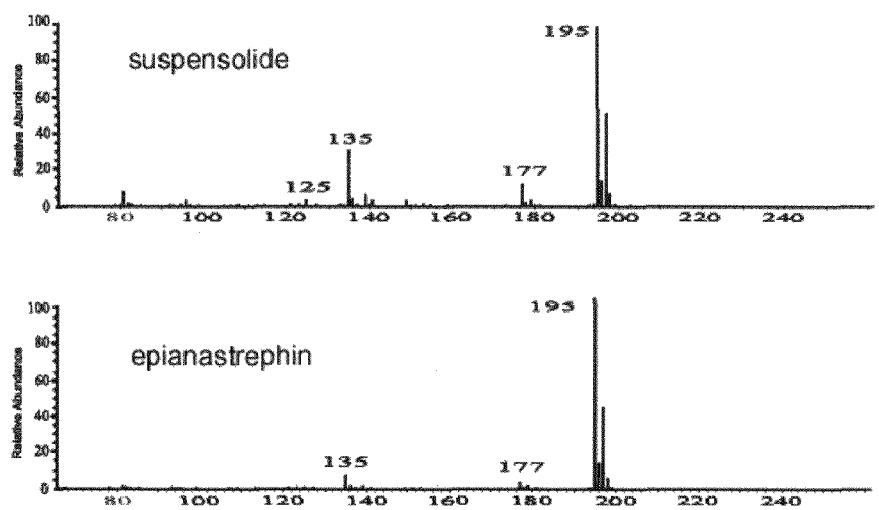
FIG. 8: A dimethyl sulfoxide solution of $^{18}$O-suspensolide (100 ng/µL), labeled at the carbonyl position, was topically applied to the cuticle overlying the salivary glands of 14-day old adult males. Three hours after application, $^{18}$O incorporation was clearly visible in the mass spectra of gas-chromatographed hexane extracts of pheromone components from (a) salivary glands and (b) crop contents that had been dried and derivatized with $CH_2N_2$.
Figure 8:
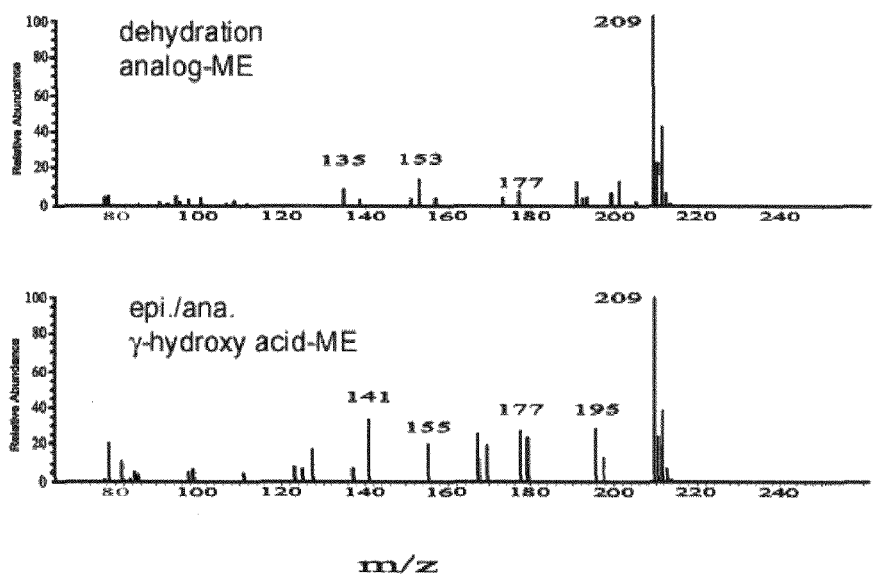
Figure 9:
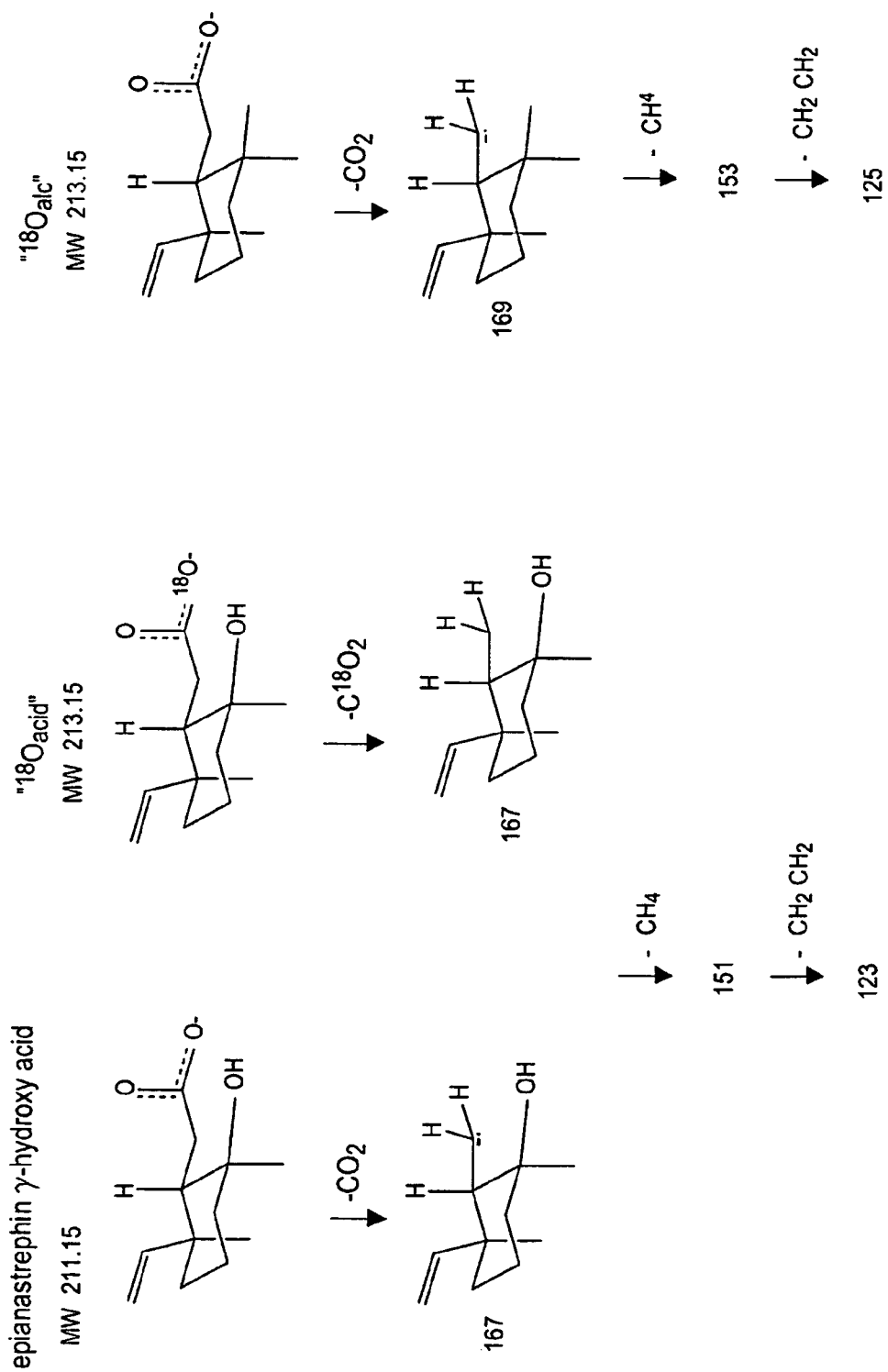
FIG. 9 shows (−)ESI HPLC-MS fragmentation schematic. (a) The γ-hydroxy acid forms of epianastrephin and anastrephin $^{18}$O mass-labeled at the acid or alcohol yielded m/z 213 [M−H]−, m/z 259 [M+H+HCOO]− or [(M−H)+ HCOOH]−, and m/z 282 [(M−H+Na)+HCOO]− or [(M−H)+ HCOONa]−, yet the m/z 213 ions of each fragmented differently. (b) The "$^{18}$O acid" yielded m/z 167 and 151 daughter ions matching the MS/MS of m/z 211 of epianastrephin hydroxy acid. (c) The "$^{18}$O alcohol" yielded m/z 169 and 153 daughter ions.
Figure 9C:
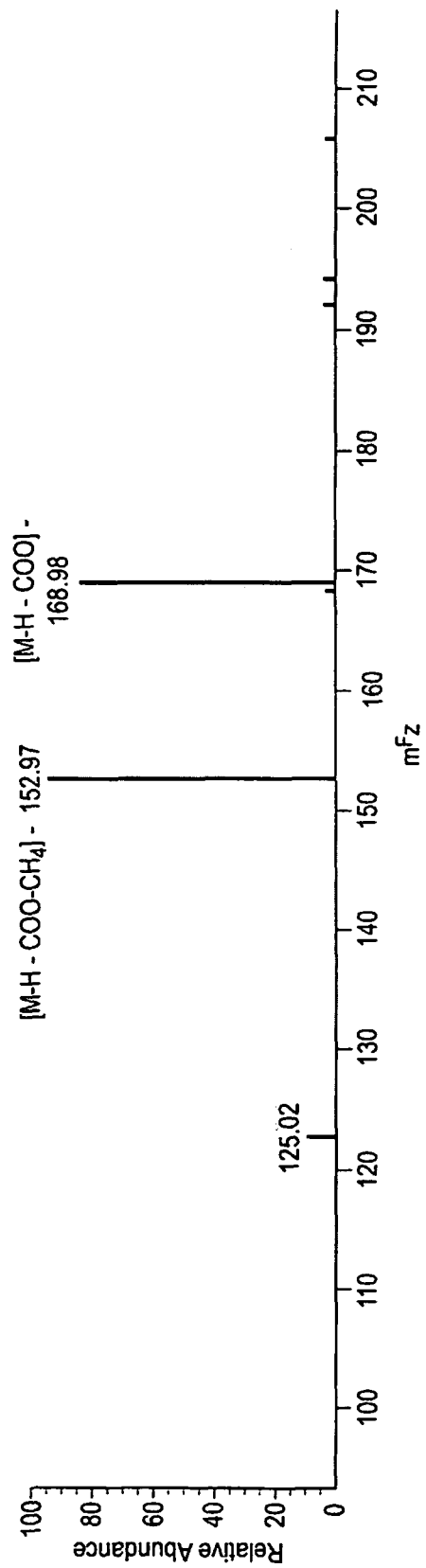
Figure 10A:
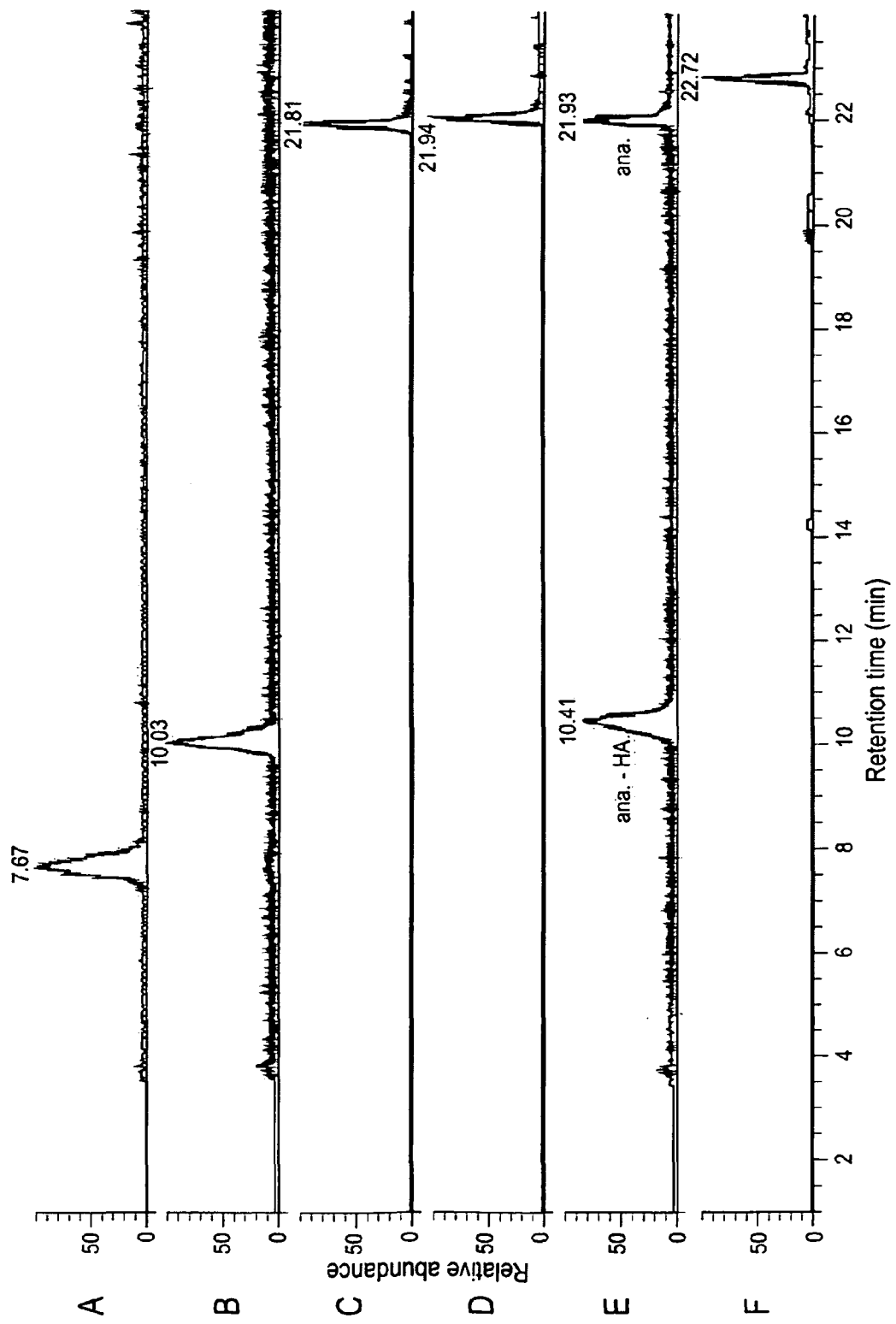
FIG. 10 shows (a) (+) ESI HPLC-MS chromatograms (m/z 195 trace): "open" sus (A), epi.-HA (B), epianastrephin (C), anastrephin (D), anastrephin hydrolysis.(E), and suspensolide (F). (b) corresponding (+) ESI m/z 60-600 mass spectra.
Figure 10B:
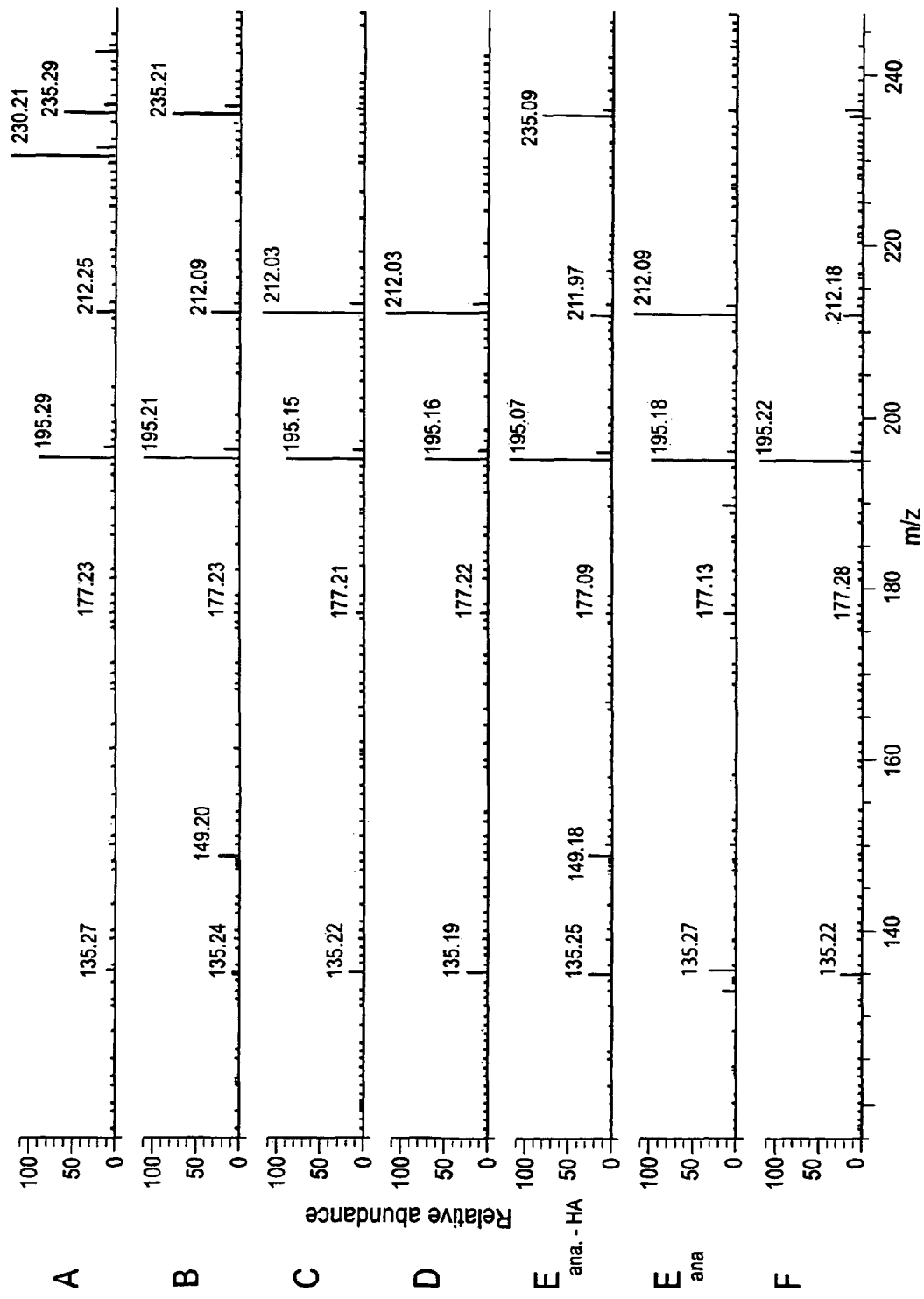
Figure 11:
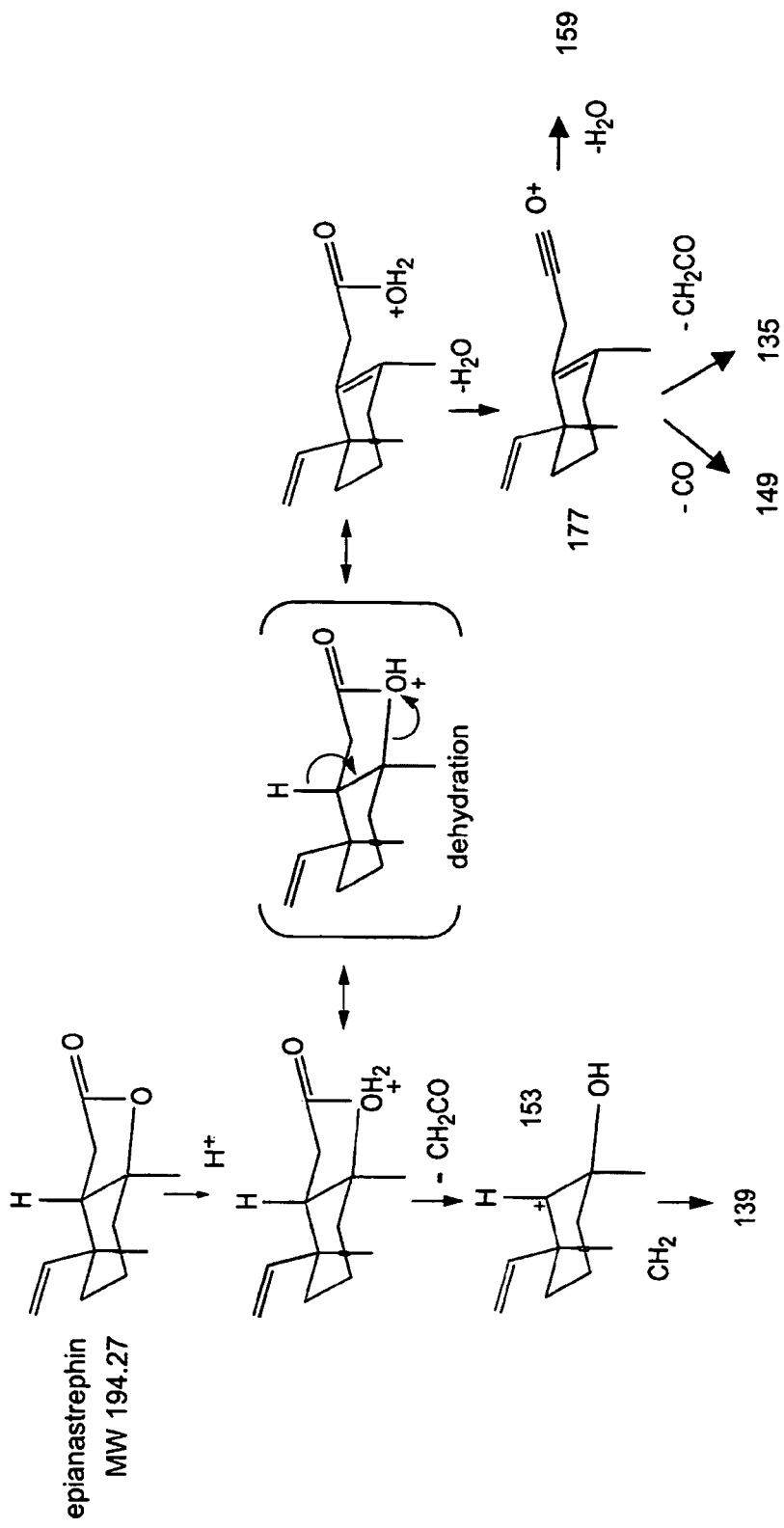
FIG. 11 shows (+)ESI-MS epianastrephin fragmentation schematic: (+)ESI-MS m/z 60-600 (A) and −MS/MS of m/z 195 (B), m/z 212 (C) and m/z 217 (D). The abundant ion-molecule reactions of the m/z 217 [M+Na]− ion with $H_2O$ yielded m/z 235 and with MeOH which yielded m/z 249 (D). Anastrephin fragmented virtually identically.
Figure 11A:
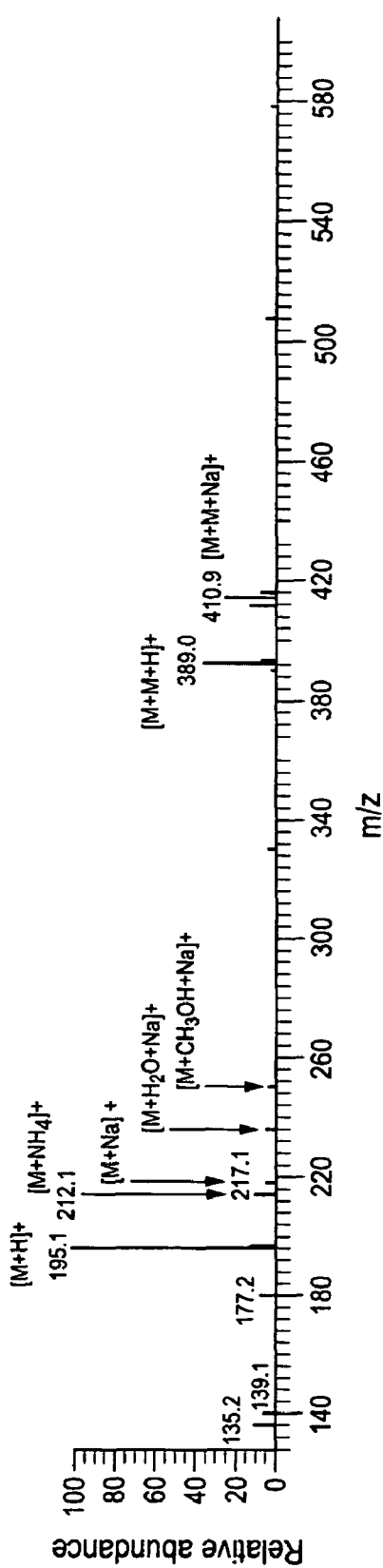
Figure 11B:
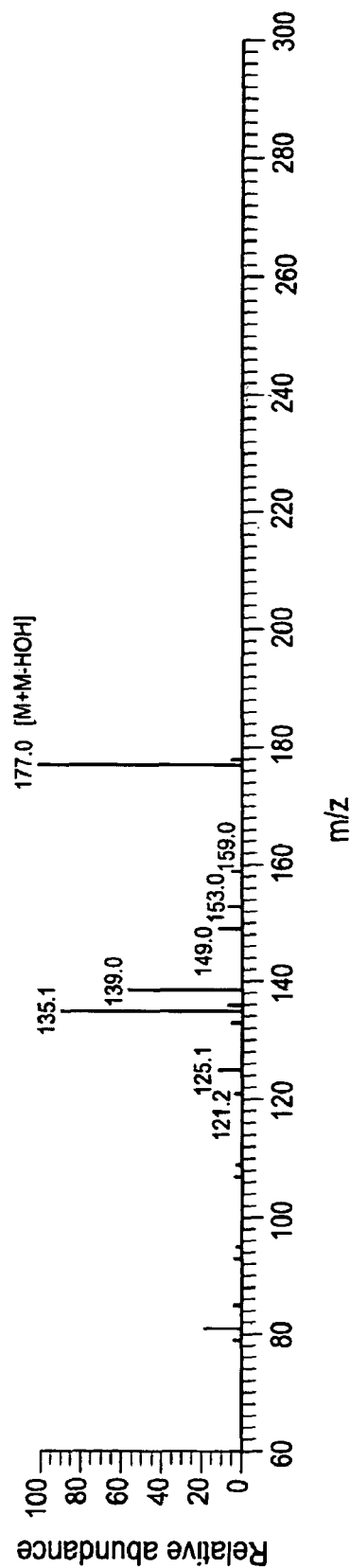
Figure 11C:
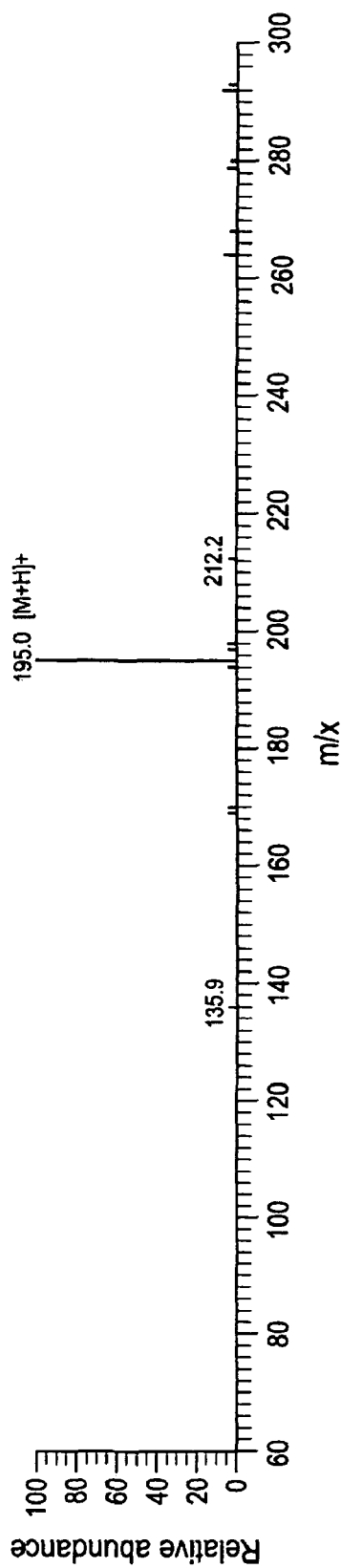
Figure 11D:
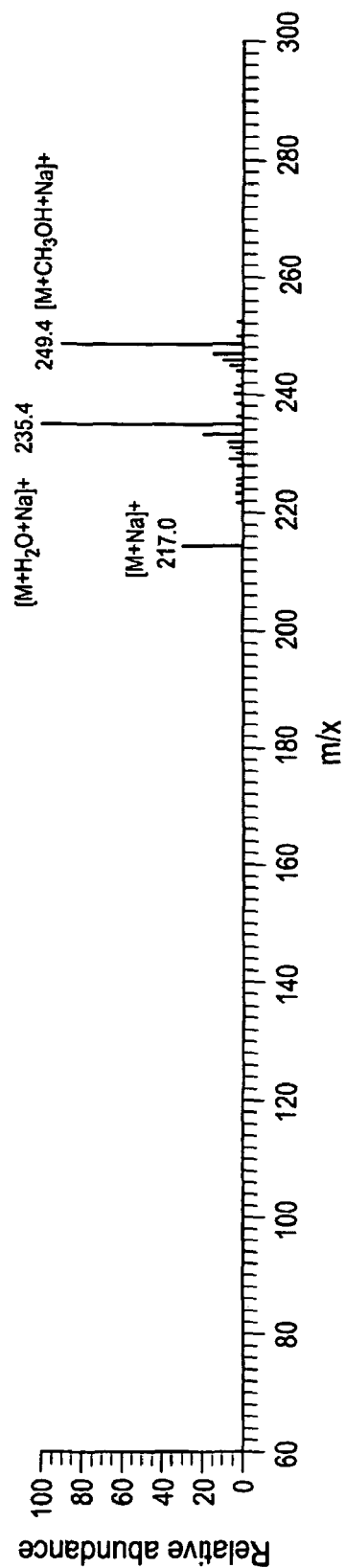
Figure 12:
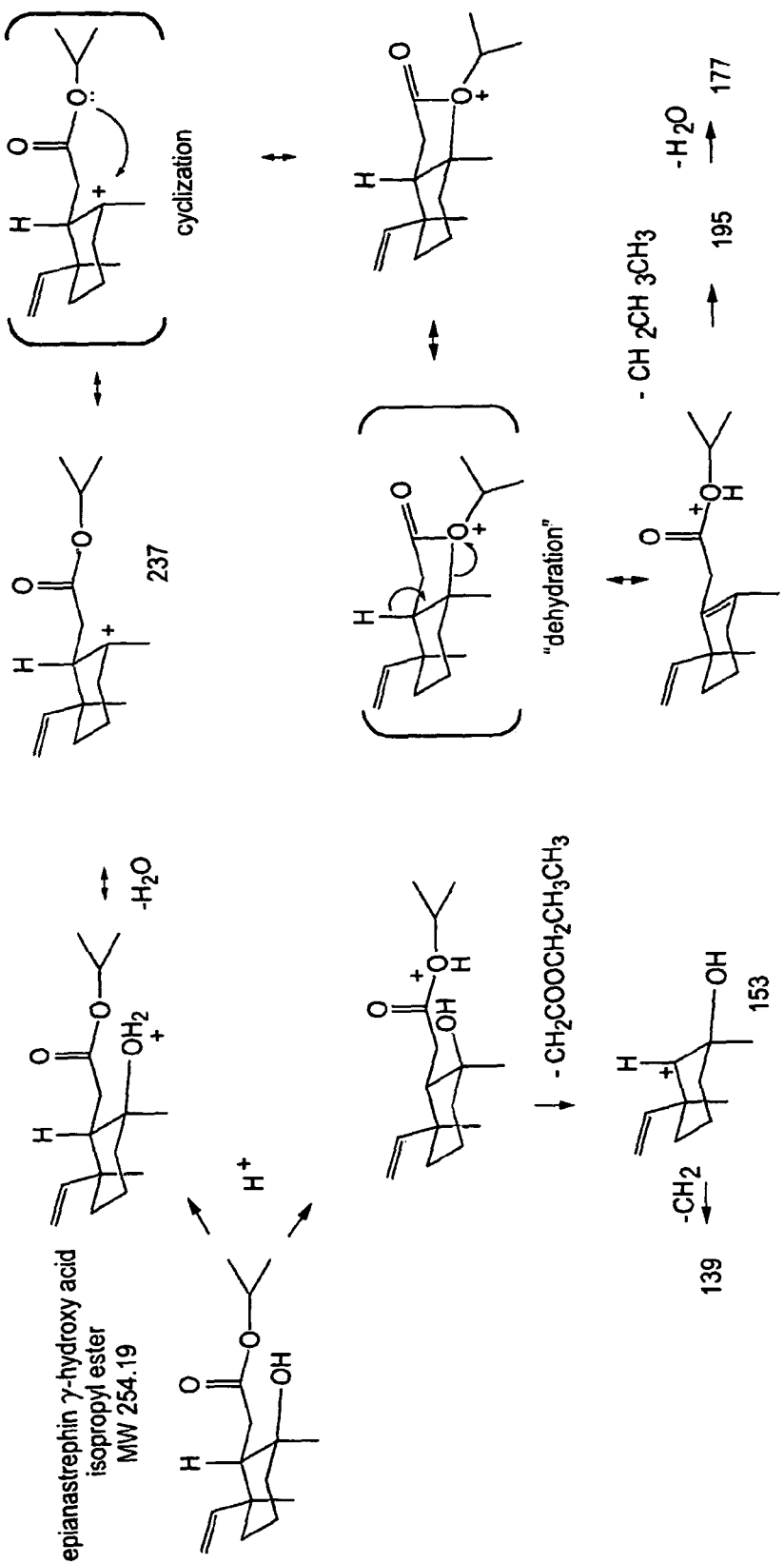
FIG. 12 shows (+)ESI-MS epianastrephin-HA isopropyl ester fragmentation schematic: Esterification was used to confirm the loss of the tertiary alcohol upon protonation. The (+)ESI-MS m/z 60-600 yielded m/z 237 [M−$H_2O_{tert}$+H]+ as most abundant with a lower abundance of m/z 255 [M+H]+ (A). The MS/MS of m/z 237 yielded m/z 195 (B). The MS/MS/MS of the m/z (237→195) ions (C) matched FIG. 10 "B" and the MS/MS/MS of the m/z (195→177) ions (D) matched those of epianastrephin and anastrephin (see FIG. 10 schematic).
Figure 12C:
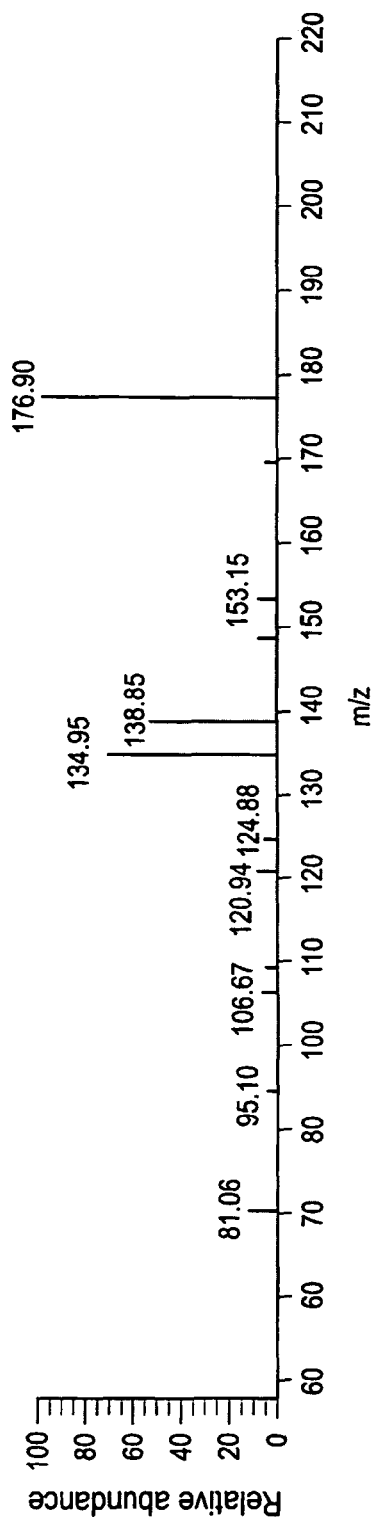
Figure 12D:
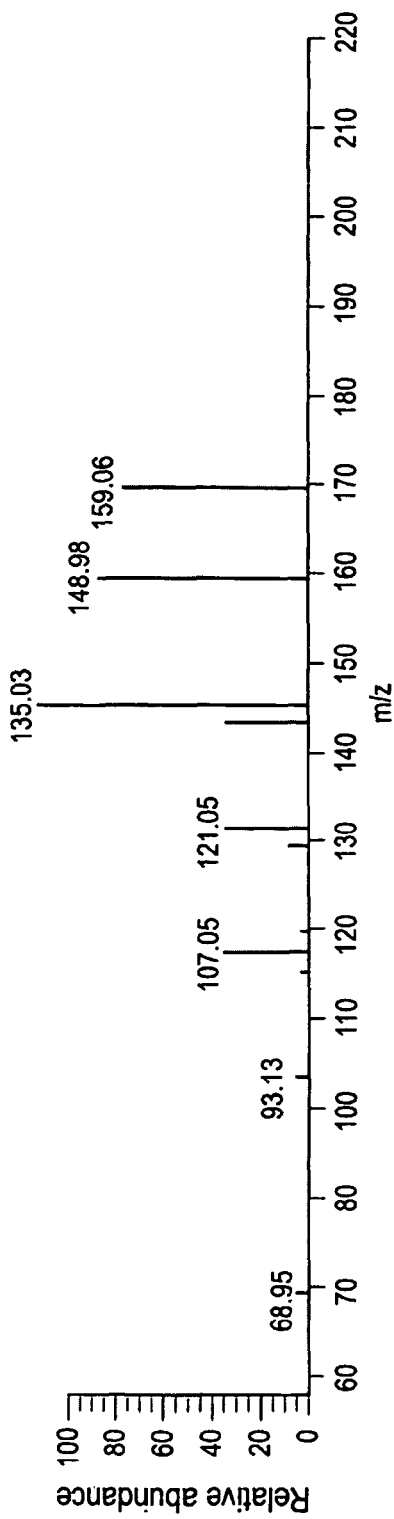
Figure 13:
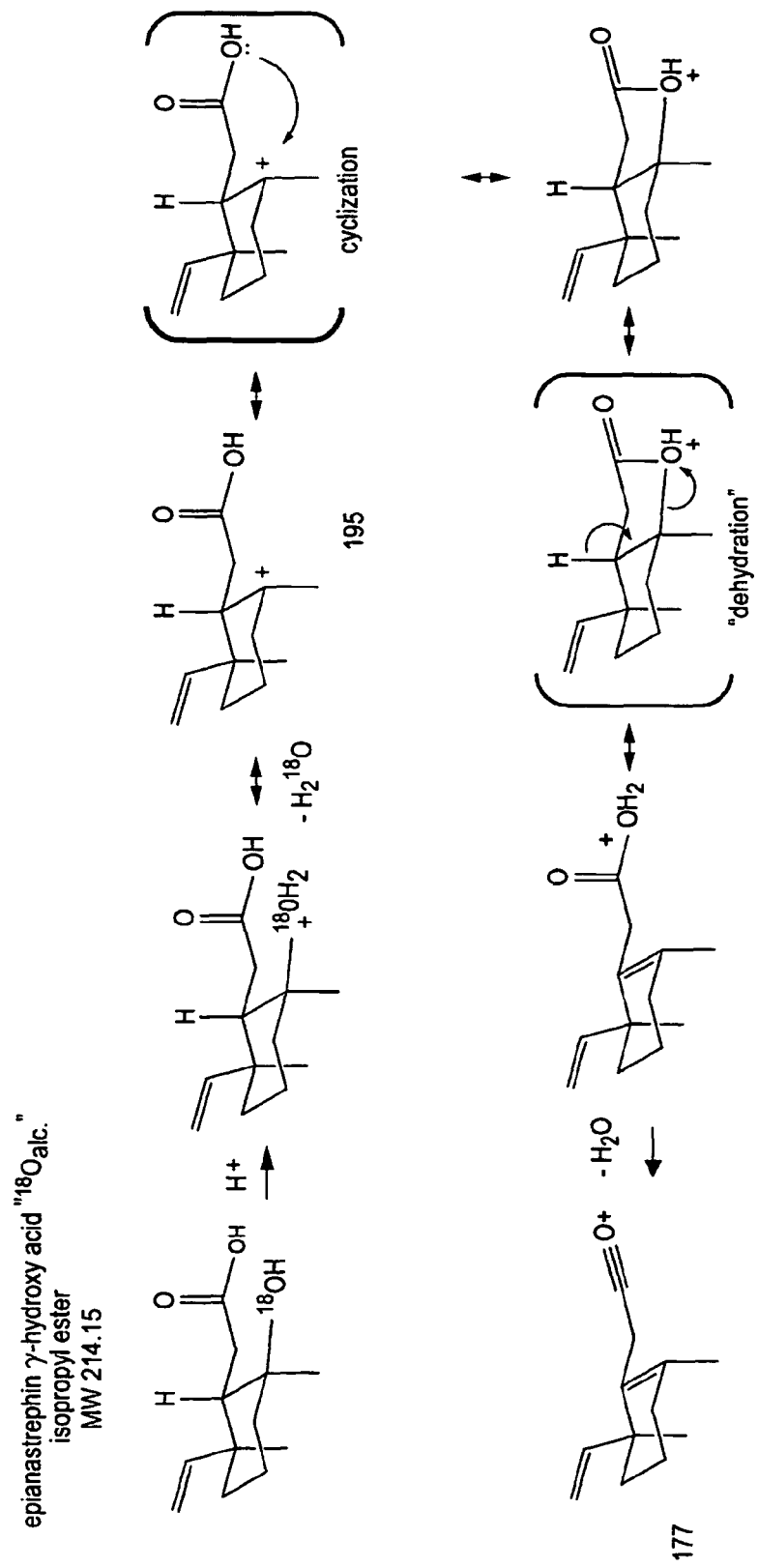
FIG. 13: Suspensolide hydrolysis in $^{18}OH_2$ at pH 5 yielded ~2.5 epianastrephin to anastrephin ratio of their γ-hydroxy acids $^{18}$O mass-labeled at the tertiary alcohol. A (+)ESI-MS m/z 212 trace was shown in addition to a fragmentation schematic. The (+)ESI-MS m/z 60-600 yielded m/z 212 [M−$H_2^{18}O_{alc.}$+$NH_4$]+ as most abundant, with lower abundances of m/z 195 [M−$H_2^{18}O_{alc.}$+H]+, 217 [M−$H_2^{18}O_{alc.}$+Na]+, and 232 [M+$NH_4$]+.
Figure 13A:
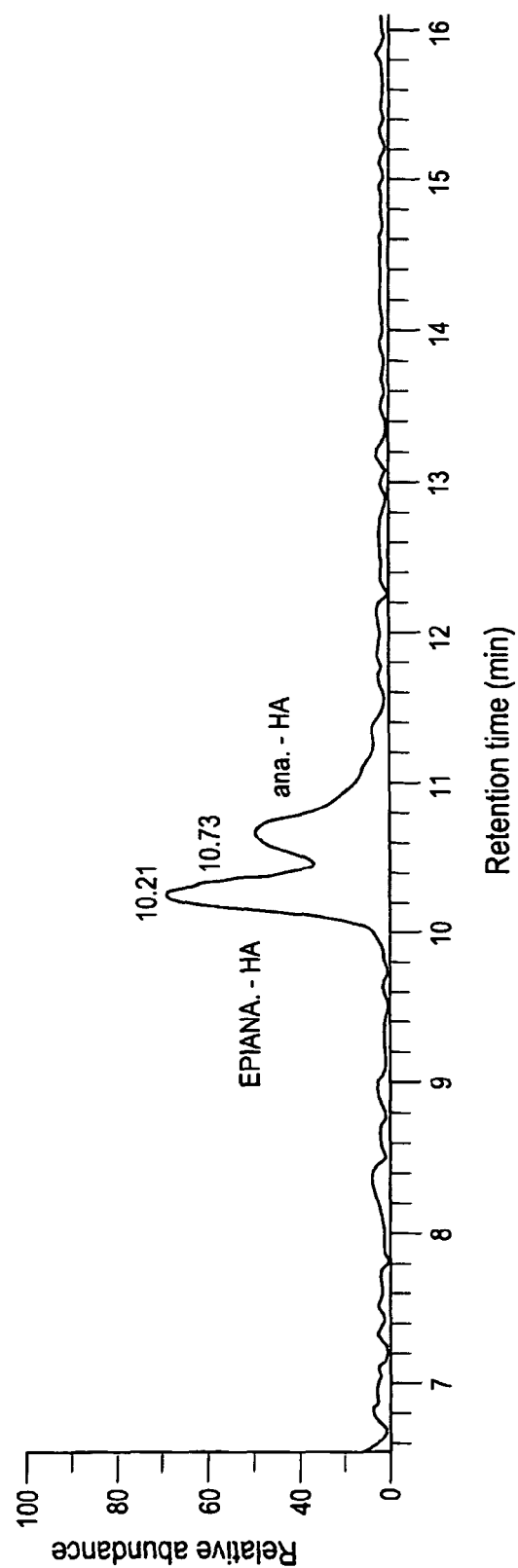
Figure 13B:
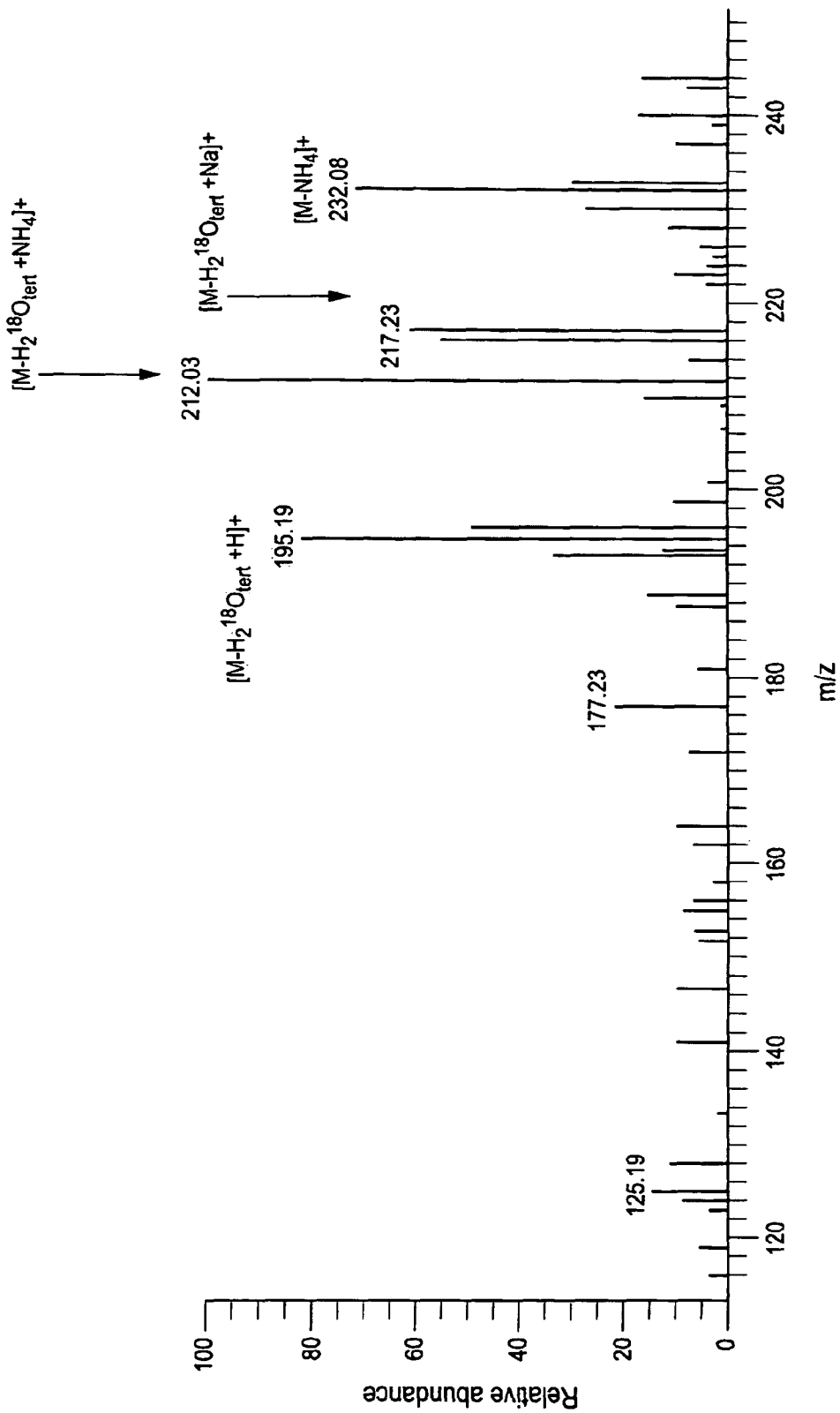
Figure 14:
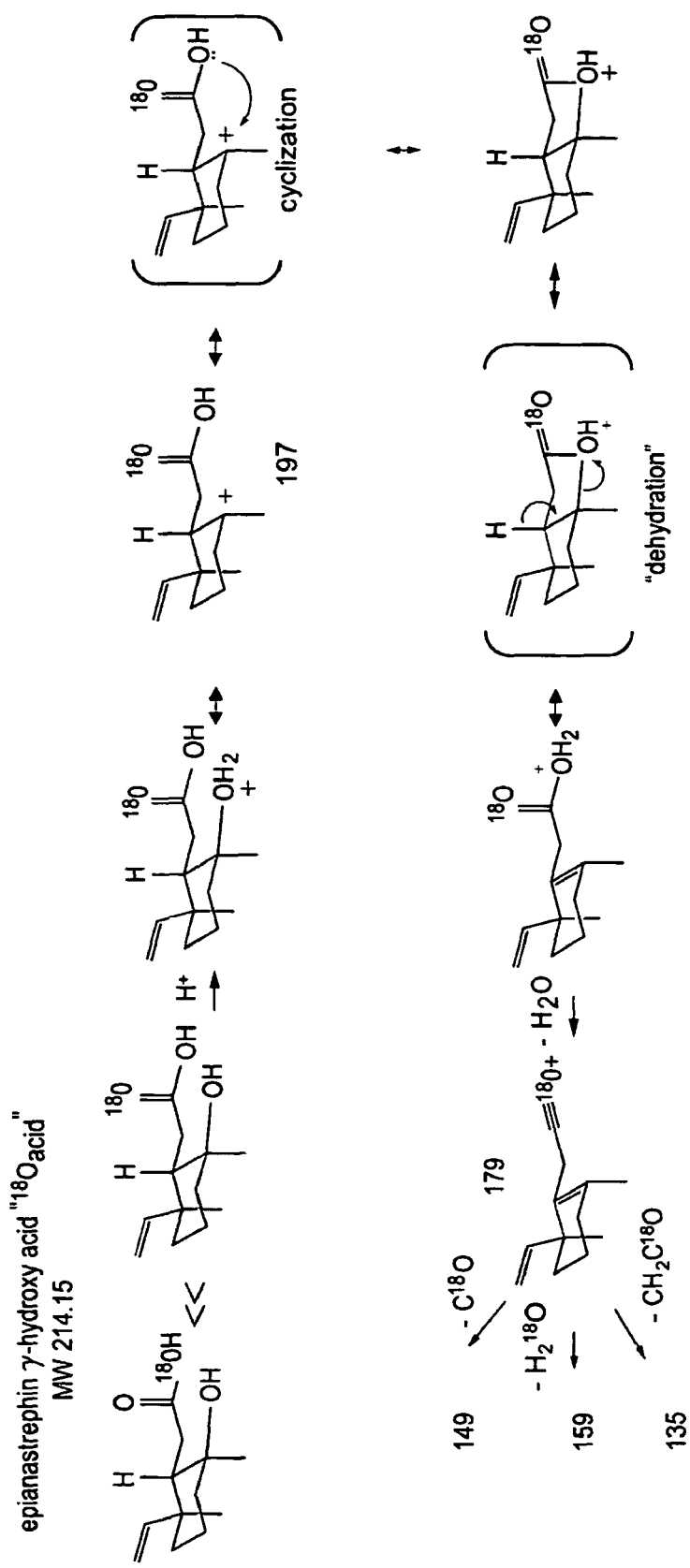
FIG. 14 shows (+)ESI-MS epianastrephin γ-hydroxy acid, $^{18}$O mass-labeled at the acid, fragmentation schematic: The (+)ESI-MS m/z 60-600 of the base-catalyzed hydrolysis product of epianastrephin in $^{18}OH_2$ yielded a m/z 232 [M+H]+ as most abundant, with lower abundances of m/z 197 [M−$H_2O_{tert.}$+H]+ and m/z 214 [M−$H_2O_{tert.}$+$NH_4$]+ (A). The MS/MS/MS of the m/z (214→197) ions (B) shows that $^{18}$O was present in the acylium ion and the MS/MS/MS of the m/z (197→179) ions (C) matched those of FIG. 11 "D".
Figure 14A:
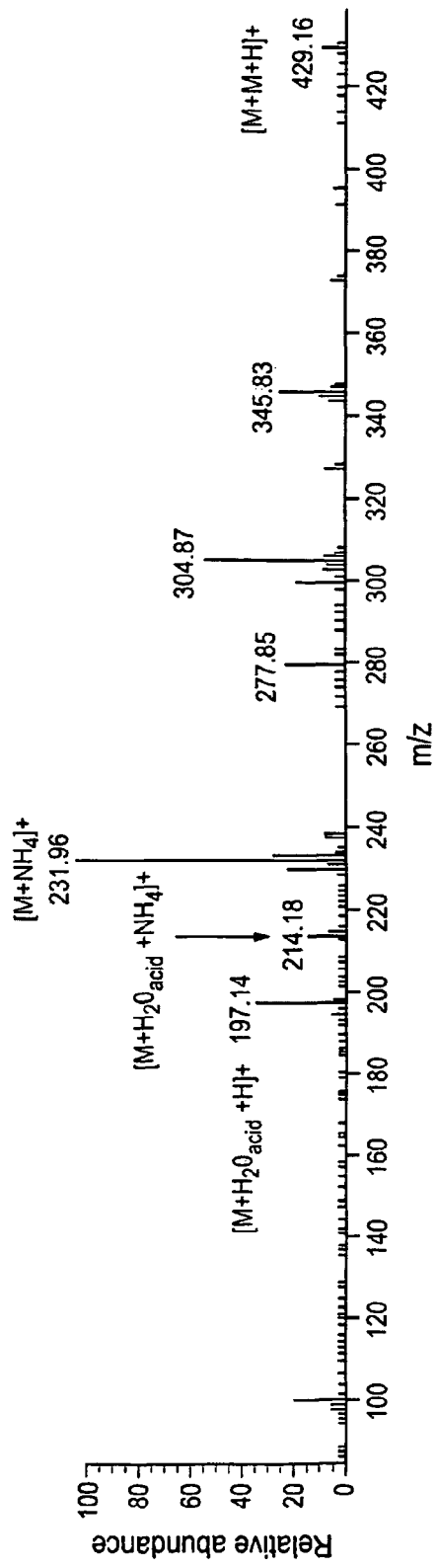
Figure 14B:
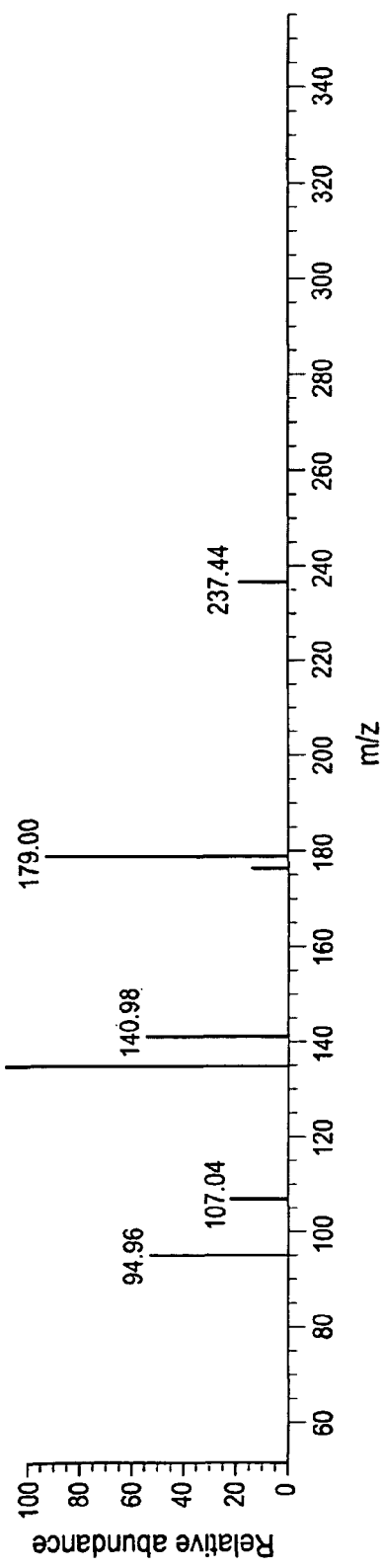
Figure 14C:
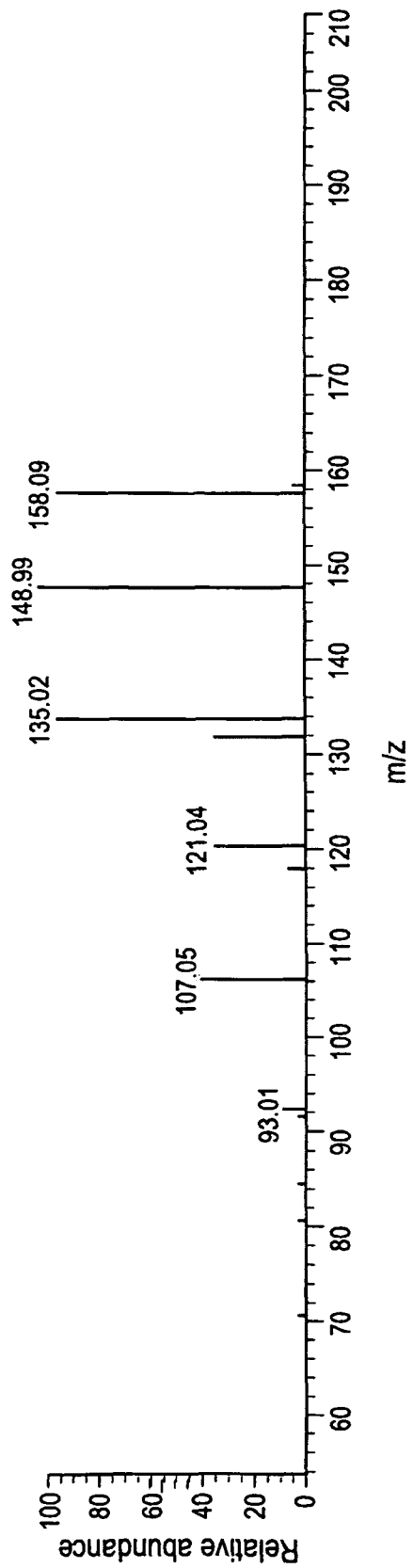

Five sexually mature (12-14 day old) flies were released into the tunnels between 22:00 and 23:00 h. Glass slides, onto which 10 μL oral secretion substrate had been deposited 24 h earlier, were inserted into the glass chambers at 04:00 h. All flies, captured or not, were removed a day after their release and the flight tunnels were wiped clean with 1:1 methanol/water in preparation for the next assay. Flies were presented a choice between volatiles emitted from male oral secretions or synthetic solutions having the sugar content found in fresh oral secretions. Synthetic sugar solutions functioned as a blank since attraction analyzed using a paired t-test revealed significant difference: female response, t=8.1, 7df, P=0.0; and male response, t=6.5, 7df, P=0.0. Other tests compared male oral secretions to synthetic sugar solutions seeded with suspensolide at a concentration that produces the naturally occurring amount of hydrolysis products (FIG. 7).

Volatile collections, used to verify equivalent volatile emission of epianastrephin and anastrephin across comparisons, were conducted in the greenhouse using glass chambers and an ambient air supply identical to those used for bioassays. Volatile collection filters containing 20 mg of Super-Q adsorbent (Altech®) were attached to the outports of the chambers and removed at the same time as the number of flies captured in traps in the flight tunnel bioassays (see above) were counted. Chemicals were eluted from volatile collection filters by flushing them with 3 ml of methyl tert-butyl ether (MTBE) into 10-mL volumetric vials precharged with 0.5 mL MTBE containing 0.4 mL of tetradecane. The eluant was then reduced to 0.5 mL with a gentle $N_2$ gas stream and used for quantitative and qualitative chemical analyses via GC-ITMS. Collection efficiencies of synthetic pheromone standards applied to the filters were >98%.

Figure 5A:
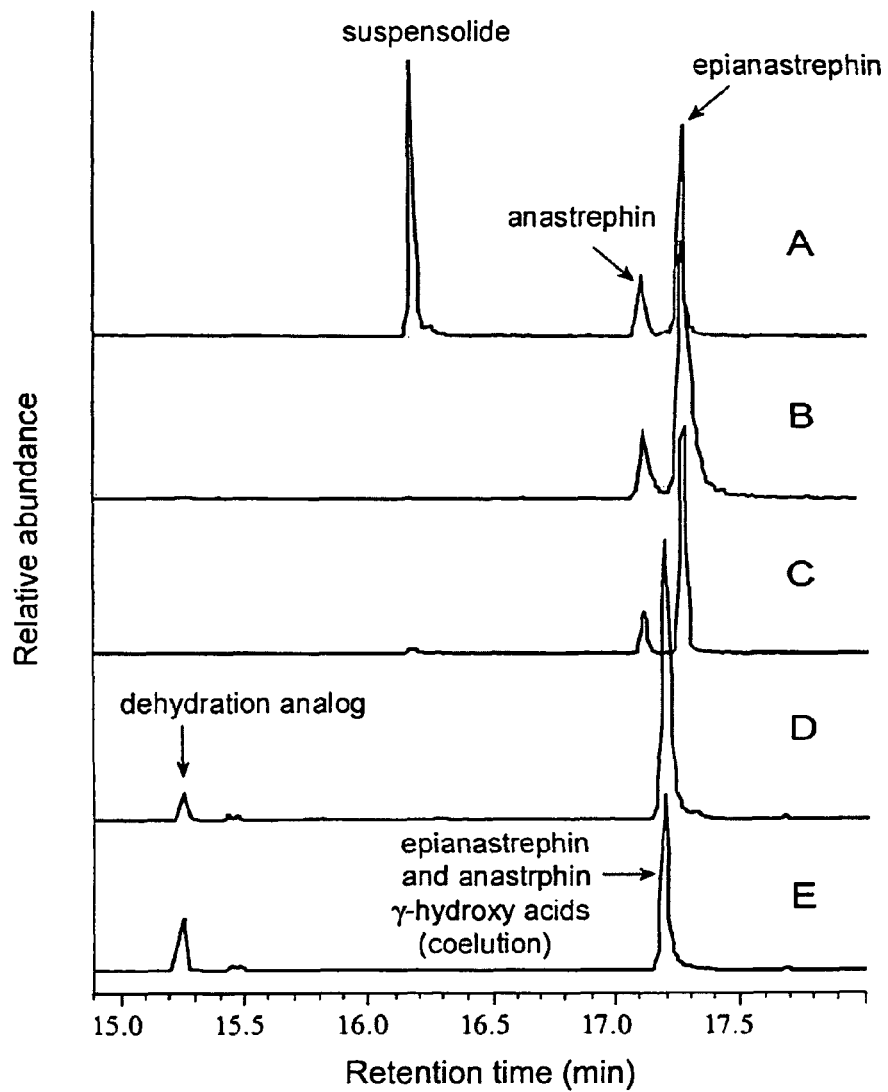
FIG. 5 shows: (a) GC-CIMS ion traces (A, B, C: m/z 195; D,E: m/z 209) of pheromone components in pentane extracts and (b) a schematic of how each was processed. Since chromatographs B≅C and D≅E, these results suggested that the abiotic hydrolysis of suspensolide occurred after phase transfer from the lipidic salivary glands of these flies. Physiological evidence provided further support as the salivary glands are connected to the water-filled crop and gut by a series of interconnected ducts.
Figure 5B:
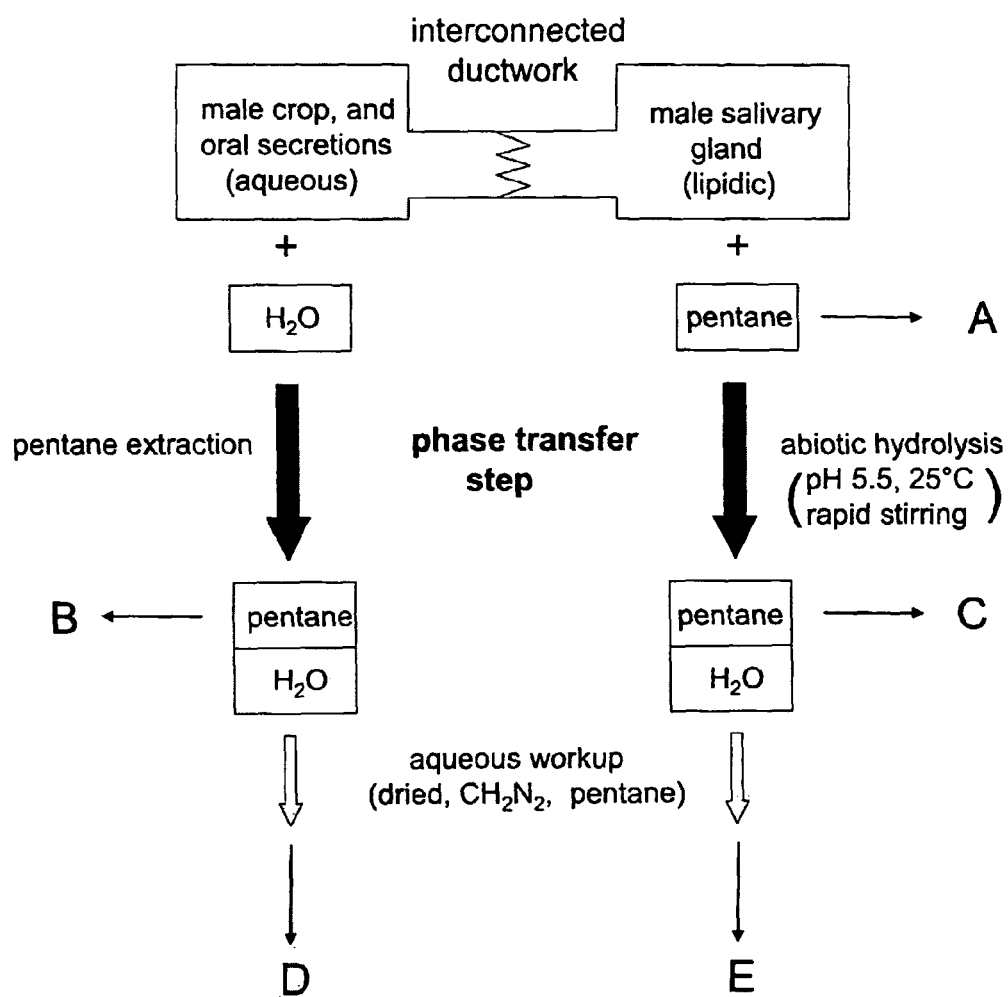
Figure 6:
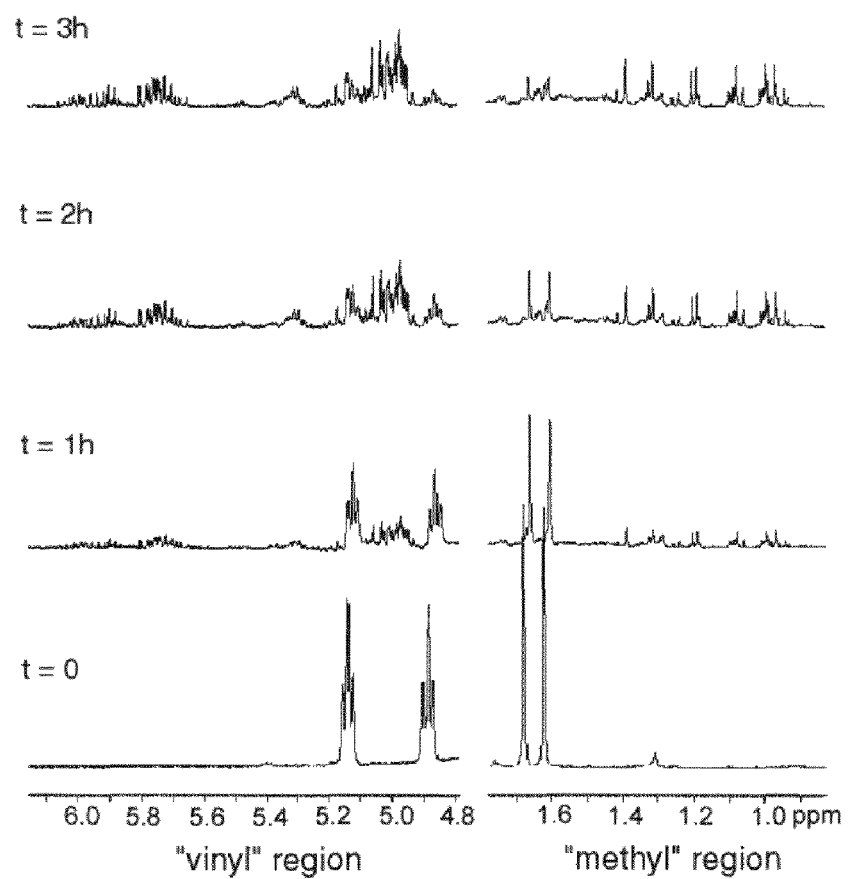
FIG. 6 shows that, monitored with $^{1}$H-NMR, suspensolide in 36 μL acetonitrile-$d_3$ (t=0) was hydrolyzed over ~3 h by the addition of 4 μl $D_2O$; the disappearance of suspensolide's vinyl and methyl protons was diagnostic of the reaction. Experiments were performed in a 2.0 mm capillary at 27° C. using a Bruker Avance 500 Console, Magnex 11.75 T/54 mm Magnet, and a 2.5 mm TXI probe (non spun). Spectra (64 scans) were acquired with 2.5 acquisition time and processed with ½ Hz line broadening.

Results and Discussion: Pentane extracts of male salivary glands that were added to water (pH 5.5) and rapidly stirred for 5 min at 25° C. yielded products within both phases that matched those obtained from pentane extraction of crops and oral secretions (FIG. 5). $^1$H-Nuclear Magnetic Resonance (NMR) spectroscopy was then employed to directly observe the hydrolysis; the original vinyl and methyl proton signals disappeared over 3 h after a 4 μL addition of $D_2O$ to suspensolide in 36 μL acetonitrile-$d_3$ (FIG. 6). In comparison, the loss of suspensolide in batch hydrolysis studies occurred much more rapidly (<2 min) over pH 3-10.

Liquid chromatography (LC) and gas chromatography (GC), coupled to mass spectroscopy (MS), were used to characterize the products of suspensolide hydrolysis (table 2). Collectively, they showed that the "closed-ring" γ-lactone and "open-ring" γ-hydroxy acid forms of epianastrephin and anastrephin, as well as a shared dehydrated form, were created rapidly and were not artifacts of subsequent aqueous interconversions that occur on relatively slow timescales. The structures of these products supported a mechanism of acid-catalyzed rearrangement. Elimination (E1) resulted in the formation of a dehydration analog, while direct intra- or intermolecular nucleophilic attack resulted in the formation of the γ-lactone or γ-hydroxy acid forms, respectively. Experiments in $H_2^{18}O$ were used to validate this interpretation (FIGS. 9-14).

Initial distributions of the major abiotic hydrolysis products of suspensolide over pH 5-6 were consistent with those observed in fresh oral secretions (pH 5.7±0.5, $\bar{x}\pm s$). Since the agreement between "natural" and synthetic product distribution is atypical within polyene biomimetic cyclizations, they are often used to diagnose enzymatic contributions within physiological systems. Although disproving their occurrence was not plausible when considering this paradigm, the finding that suspensolide rearrangement was initiated by water raised doubt about enzymatic catalysis in this particular instance.

In order to demonstrate the importance of suspensolide lipid to water phase transfer to caribflies, the biological role and chemical inter-conversion of the hydrolysis products had to be understood. Our investigations provided the necessary insight. The deposition of oral secretions at lek mating sites was found to attract both sexes due to the diffusion-limited release rate of epianastrephin and anastrephin from the scent marks. The emission of these pheromones, which occurs for many days as a function of humidity and temperature, was linked to aqueous equilibrium between their γ-hydroxy acids and their thermodynamically less preferred (~1:100), but relatively volatile, γ-lactone equivalents. We also found that synthetic sugar-solutions seeded with suspensolide were surprisingly equally attractive to both sexes as male oral secretions within a previously described flight-tunnel bioassay system (FIG. 7).

All of the references cited herein, including U.S. Patents, are incorporated by reference in their entirety. Also incorporated by reference in their entirety are the following references: Alvarez-Manzaneda, E. J., et al., Tetrahedron Lett., 45: 4453-4455 (2004); Baker, J., and R. R. Heath, J. Chem. Ecol., 19: 1511-1519 (1993); Battiste, M. A., et al., Tetrahedron Lett. 24:2611-2614 (1983); Battiste, M. A., et al., Tetrahedron Lett., 29: 6565-6568 (1988); Battiste, M. A., et al., Tetrahedron Lett., 32: 5303-5304 (1991); Battiste, M. A., et al., J. Org. Chem., 61: 6454-6455 (1996); Burk, T., Fla. Entomol., 65: 90-104 (1982); Burk, T., Fla. Entomol., 66: 330-343 (1983); Burk, T., Florida Entomologist, 66: 330-344 (1983); Carslaw, H. S., and J. C. Jaeger, Conduction of heat in Solids, Oxford University Press, London, 1959; Crank, J., The mathematics of Diffusion, Oxford University Press, London, 1975; EPI-Suite, WATERNT v1.00, U.S.E.P.A., 2002; Chuman, T., et al., Tetrahedron Lett., 29(50): 6561-6564 (1988); Epsky, N. D., and R. R. Heath, Environ. Entomol., 22: 464-469 (1993); Epsky, N. D., and R. R. Heath, Environ. Entomol., 22: 942-947 (1993); Epsky, N. D., et al., Fla. Entomol., 76: 626-635 (1993); Govindaraju, V., et al., NMR Biomed., 13: 129-153 (2000); Harwood, L. M., and C. J. Moody, Experimental Organic Chemistry: Principles and Practice, Blackwell Scientific Publications, Oxford, UK, 1989; Heath, R. R., et al., J. Chem. Ecol., 18: 441-453 (1992); Heath, R. R., et al., J. Chem. Ecol., 19: 2395-2410 (1993); Heath, R. R., et al., Fla. Entomol., 76: 233-244 (1993); Hendrichs, H., 1986, Sexual selection in wild and sterile Caribbean fruit flies, *Anastrepha suspensa* (Leow) (Diptera: Tephritidae), M.Sc. Thesis, University of Florida, Gainesville, Florida; Hendrix, D. L., Crop Science, 33: 1306-1311 (1993); Hendrichs, M. A., J. Hendrichs, Ann. Entomol. Soc. Am., 83: 228-234 (1998); Hopke, J., et al., FEBS Lett., 352: 146-150 (1994); Ikura, M., and K. Hikichi, Carbohydrate Research, 163:1-8 (1987); Johnson, W. S., Bioorganic Chemistry, 5: 51-98 (1976); Landolt, P. J., and J. Sivinski, Environ. Entomol., 21: 382-387 (1982); Lu, F., and P. E. A. Teal, Arch. Insect. Biochem. Physiol., 48: 144-154 (2001); Mattiacci, L., et al., Proc. Natl. Acad. Sci. U.S.A., 92: 2036-2040 (1995); Mori, K., and Y. Nakazono, Liebigs. Ann. Chem., 167-174 (1988); Nation, J. L., Ann. Entomol. Soc. Am., 65: 1364-1367 (1972); Nation, J. L., Ann. Entomol. Soc. Am., 67: 731-734 (1974); Nation, J. L., Environ. Entomol., 4: 27-30 (1975); Nation, J. L., Int. J. Insect Morphol. & Embryol., 10: 121-129 (1981); Nation, J. L., 1989, The role of pheromones in the mating system of *Anastrepha* fruit flies, pp. 189-205, In: A. S. Robinson and G. Hooper (eds.), World Crop Pests, Volume 3A, Fruit flies, their biology, natural enemies and control, Elsevier, NY; Nation, J. L., J. Chem. Ecol., 16: 553-572 (1990); Nation, J. L., 1991, Sex pheromone components of *Anastrepha suspensa* and their role in mating behavior, pp. 224-236, In: K. Kawasaki, O. Iwahashi and K. Y. Kaneshiro (eds.), Proceedings of the International Symposium on the Biology and Control of Fruit Flies. Ginowan, Okinawa, Japan; Norrbom, A. L., R. C. Foote, In: Fruit Flies Their biology, natural enemies, and control, eds. Robinson, A. S, and Hooper, G., 15-26 (Elsevier, 1989); Perdomo, A. J., 1974, Sex and aggregation bioassays and mating observations of the Caribbean fruit fly under field conditions, Ph.D. Thesis, Univ. Fla., Gainesville, Florida; Perdomo, A. J., et al., Fl. Entomol., 58: 291-295 (1975); Perdomo, A. J., et al., Environ. Entomol., 5:1208-1210 (1976); Rocca, J. R., et al., J. Chem. Ecol., 18: 223-244 (1992); Saito, A., et al., Chemistry Lett., 729-730 (1984); Shelly, T. E., and T. S. Whittier, The evolution of mating systems in insects and Arachnids, eds. Crespi, B. & J. C. Choe, Cambridge Press, Cambridge, UK, 1997; Sivinski, J., J. Insect Behav., 2: 3-13 (1989); Sivinski, J. M., and T. Burk, Reproductive and mating behavior, In: World Crop Pests, Volume 3A, Fruit flies, their biology, natural enemies and control, eds. Robinson, A. S., and G. Hooper, pages 343-350, Elsevier, 1989; Sivinski, J., and J. C. Webb, Ann. Entomol. Soc. Am., 79: 146-149 (1986); Sivinski, J. M., et al., J. Insect Behav., 7: 43-51 (1994); Sivinski, J., et al., Fruit flies (Tephritidae): Phylogeny and evolution of behavior, eds. M. Aluja and A. L. Norrbom, pages 751-792, CRC, Boca Raton, Fla., 2000; Skoog, D., and J. Leary, J. Principles of Instrumental Analysis (1992); Strekowski, L., and M. E. Battiste, *Tetrahedron Lett.,* 22: 279-282 (1981); Tadano, K., et al., J. Org. Chem., 58: 6266-6279 (1993); Teal, P. E. A., and F. Lu, Arch. Insect Biochem. Physiol., 48: 144-154 (2001); Teal, P. E. A., et al., Anal. Biochem., 277: 206-213 (2000); Thornhill, R., Fla. Entomol., 63: 5-30 (1980); Thornhill, R., et al., Am. Biol. Teacher, 45: 310-319 (1983); Tumlinson, J. H., J. Chem. Ecol., 14: 2109-2130 (1988); Webb, J. C., et al., Annals Entomol. Soc. Am., 76: 996-998 (1983); Wilson, E. O., Sociobiology: the new synthesis, Harvard University Press, Cambridge, Mass., 1975; Wydra, R. L., et al., Tetrahedron, 48: 3485-3494 (1992); Yoder, R. A., and J. N. Johnston, Chem. Rev., 105: 4730-4756 (2005);

Molinspiration Cheminformatics, miLogP2.2 (2005), http://www.molinspiration.com/services/logp.html Thus, in view of the above, the present invention concerns (in part) the following:

A composition (for attracting *Anastrepha* species like *A. suspensa*) comprising (or consisting essentially of or consisting of) suspensolide and optionally at least one member of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a carrier or carrier material; said composition containing no β-bisabolene and no α-farnesene. The above composition comprising an aqueous solution of about 200 μM (e.g., 200 μM) suspensolide in a water solution (containing about 25 weight % (e.g., about 25 weight %) sugar).

The above composition, further comprising at least one member of the group consisting of γ-lactone of epianastrephin, γ-lactone of anastrephin, and mixtures thereof.

The above composition, said composition containing no (Z)-3-nonen-1-ol, no (Z,Z)-3,6-nanadien-1-ol, and no (Z)-β-ocimene.

The above composition, said composition containing γ-hydroxy acid of epianastrephin.

The above composition, said composition containing no γ-hydroxy acid of epianastrephin.

The above composition, said composition containing γ-hydroxy acid of anastrephin.

The above composition, said composition containing no γ-hydroxy acid of anastrephin.

The above composition, said composition containing 2,6-dimethyl-6-vinyl-cyclohexeneacetic acid.

The above composition, said composition containing no 2,6-dimethyl-6-vinyl-cyclohexeneacetic acid.

The above composition, said composition containing β-D-glucopyranosyl 2,6-dimethyl-6-vinyl-cyclohex-1-ene-1-acetoate.

The above composition, said composition containing no β-D-glucopyranosyl 2,6-dimethyl-6-vinyl-cyclohex-1-ene-1-acetoate.

The above composition, said composition containing suspensolide and γ-hydroxy acid of epianastrephin.

The above composition, said composition containing suspensolide and γ-hydroxy acid of anastrephin.

The above composition, said composition containing γ-hydroxy acid of anastrephin and γ-hydroxy acid of epianastrephin.

The above composition, said composition containing suspensolide, γ-hydroxy acid of epianastrephin, and γ-hydroxy acid of anastrephin.

The above composition, said composition containing γ-lactone of epianastrephin.

The above composition, said composition containing no γ-lactone of epianastrephin.

The above composition, said composition containing γ-lactone of anastrephin.

The above composition, said composition containing no γ-lactone of anastrephin.

The above composition, said composition containing γ-lactone of epianastrephin and γ-lactone of anastrephin.

The above composition, said composition containing no γ-lactone of epianastrephin and no γ-lactone of anastrephin.

The above composition, said composition containing a carrier or carrier material. The above composition, wherein said carrier is water. The above composition, wherein said carrier is a sugar solution (aqueous) containing at least fructose or sucrose or both.

The above composition, said composition comprising (or consisting essentially of or consisting of) suspensolide and optionally at least two members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a carrier or carrier material; said composition containing no β-bisabolene and no β-farnesene.

The above composition, said composition comprising (or consisting essentially of or consisting of) suspensolide and optionally at least three members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a carrier or carrier material; said composition containing no β-bisabolene and no α-farnesene.

The above composition, said composition comprising (or consisting essentially of or consisting of) suspensolide, γ-hydroxy acid of epianastrephin, γ-hydroxy acid of anastrephin, and 2,6-dimethyl-6-vinyl-cyclohexeneacetic acid, β-D-glucopyranosyl 2,6-dimethyl-6-vinyl-cyclohex-1-ene-1-acetoate, and optionally a carrier or carrier material; said composition containing no β-bisabolene and no α-farnesene.

A method for attracting *Anastrepha suspensa*, said method comprising (or consisting essentially of or consisting of) treating an object or area with an *Anastrepha suspensa* attracting effective amount of the above composition.

The above method, wherein said composition further comprises at least one member of the group consisting of γ-lactone of epianastrephin, γ-lactone of anastrephin, and mixtures thereof.

The above method, wherein said composition contains no (Z)-3-nonen-1-ol, no (Z,Z)-3,6-nanadien-1-ol, and no (Z)-β-ocimene.

The above method, wherein said composition contains γ-hydroxy acid of epianastrephin.

The above method, wherein said composition contains γ-hydroxy acid of anastrephin.

The above method, wherein said composition contains γ-hydroxy acid of epianastrephin and γ-hydroxy acid of anastrephin.

The above method, wherein said composition contains γ-lactone of epianastrephin.

The above method, wherein said composition contains γ-lactone of anastrephin.

The above method, wherein said composition contains γ-lactone of epianastrephin and γ-lactone of anastrephin.

The above method, wherein said composition contains a carrier or carrier material.

The above method, wherein said carrier comprises an aqueous solution containing at least one sugar.

The above method, wherein said sugar comprises at least one member of the group consisting of fructose, sucrose, and mixtures thereof, and optionally glucose.

The above method, wherein said aqueous solution contains a ratio of ~D-glucose: 2 D-fructose: sucrose.

The above method, wherein said *Anastrepha* species is *Anastrepha suspensa*.

The above method, wherein said *Anastrepha suspensa* are males.

The above method, wherein said *Anastrepha suspensa* are females.

The above method, wherein said *Anastrepha suspensa* are *Anastrepha suspensa* males and *Anastrepha suspensa* females.

The above method, wherein said composition contains no γ-hydroxy acid of epianastrephin.

The above method, wherein said composition contains no γ-hydroxy acid of anastrephin.

The above method, wherein said composition contains 2,6-dimethyl-6-vinyl-cyclohexeneacetic acid.

The above method, wherein said composition contains no 2,6-dimethyl-6-vinyl-cyclohexeneacetic acid.

The above method, wherein said composition contains β-D-glucopyranosyl 2,6-dimethyl-6-vinyl-cyclohex-1-ene-1-acetoate.

The above method, wherein said composition contains no β-D-glucopyranosyl 2,6-dimethyl-6-vinyl-cyclohex-1-ene-1-acetoate.

The above method, wherein said composition contains no γ-lactone of epianastrephin.

The above method, wherein said composition contains no γ-lactone of anastrephin.

The above method, wherein said composition contains about 14.3 μM (e.g., 14.3 μM) anastrephin, about 35.7 μM (e.g., 35.7 μM) epianastrephin, about 28.7 μM (e.g., 28.7 μM) γ-hydroxy acid of anastrephin, about 71.9 μM (e.g., 71.9 μM) γ-hydroxy acid of epianastrephin, about 10.8 μM (e.g., 10.8 μM) 2,6-dimethyl-6-vinyl-cyclohexeneacetic acid, and about 6.2 µM (e.g., 6.2 µM) β-D-glucopyranosyl 2,6-dimethyl-6-vinyl-cyclohex-1-ene-1-acetoate.

The above method, wherein said composition contains less than 14.3 µM anastrephin, less than 35.7 µM epianastrephin, less than 28.7 µM γ-hydroxy acid of anastrephin, less than 71.9 µM γ-hydroxy acid of epianastrephin, less than 10.8 µM 2,6-dimethyl-6-vinyl-cyclohexeneacetic acid, and less than 6.2 µM β-D-glucopyranosyl 2,6-dimethyl-6-vinyl-cyclohex-1-ene-1-acetoate.

The above method wherein the composition comprises an aqueous solution of about 172 to about 200 µM (e.g., 172-200 µM) suspensolide in a water solution (containing about 25 weight % (e.g., about 25 weight %) sugar).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

| Analyte | GC $R_T$ ±0.01 (min) | most abundant ion CIMS | method L.O.D. select-ion CI-MS ($10^{-9}$ M) |
|---|---|---|---|
| tetradecane (int-std.) | 14.64 | 199 | 5.4 ± 0.4 |
| dehydration analog - ME | 15.27 | 209 | 3.6 ± 0.2 |
| Suspensolide | 16.18 | 195 | 3.5 ± 0.2 |
| Anastrephin | 17.15 | 195 | 3.3 ± 0.2 |
| "cis-fused" anastrephin | 17.19[a] | 195 | 3.3 ± 0.2[b] |
| ana. - HA (ME) | 17.22 | 209[c] | 3.9 ± 0.3 |
| epi. - HA (ME) | 17.22 | 209[c] | 3.9 ± 0.3 |
| "cis-fused" epianastrephin | 17.27[a] | 195 | 3.4 ± 0.2[b] |
| Epianastrephin | 17.31 | 195 | 3.4 ± 0.2 |
| "open" sus. - ME[d] | 18.21 | 227 | 4.4 ± 0.5 |

[a] assignments based on Battiste et al.(J. Org. Chem., 61: 6454-6455 (1996))
[b] assumed equal to that of 7a epimer "trans-fused" equivalent
[c] note loss of tertiary alcohol upon ionization (see HPLC data)
[d] 10-hydroxy-4,8-dimethyldeca-3(E), 8(E)-dienoic acid
HA = γ-hydroxy acid, ME = methyl ester, L.O.D. = limit of detection

TABLE 2

GC-ITMS and HPLC-EIMS spectra and retention times were used to verify products. The standard deviation associated with triplicate injections was used to assess error in all concentration measurements.

| analyte | HPLC-MS $R_T$(min) | method L.O.D. (ng) (+) ESI- MS m/z 195 |
|---|---|---|
| "open" sus. | 7.65 ± 1.1 | 12 ± 3 |
| epi. - HA | 10.1 ± 1.5 | 10 ± 2 |
| ana. - HA | 10.8 ± 1.5 | 11 ± 2 |
| dehydration analog | 11.7 ± 1.7 | 95 ± 5 |
| epianastrephin | 21.8 ± 0.4 | 40 ± 2 |
| anastrephin | 21.9 ± 0.4 | 41 ± 2 |
| suspensolide | 22.7 ± 0.3 | 35 ± 1 |
| (+)-sclareolide (ext. std) | 24.4 ± 0.4 | 30 ± 3 |

We claim:

1. A method for attracting *Anastrepha* species, said method comprising treating an object or area with an *Anastrepha* species attracting effective amount of a composition comprising suspensolide and at least one member of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a carrier or carrier material; said composition containing no β-bisabolene and no α-farnesene.

2. The method according to claim 1, wherein said composition further comprises at least one member of the group consisting of γ-lactone of epianastrephin, γ-lactone of anastrephin, and mixtures thereof.

3. The method according to claim 1, wherein said composition contains no (Z)-3-nonen-1-ol, no (Z,Z)-3,6-nanadien-1-ol, and no (Z)-β-ocimene.

4. The method according to claim 1, wherein said composition contains γ-hydroxy acid of epianastrephin.

5. The method according to claim 1, wherein said composition contains γ-hydroxy acid of anastrephin.

6. The method according to claim 1, wherein said composition contains γ-hydroxy acid of epianastrephin and γ-hydroxy acid of anastrephin.

7. The method according to claim 1, wherein said composition contains γ-lactone of epianastrephin.

8. The method according to claim 1, wherein said composition contains γ-lactone of anastrephin.

9. The method according to claim 1, wherein said composition contains γ-lactone of epianastrephin and γ-lactone of anastrephin.

10. The method according to claim 1, wherein said composition contains a carrier or carrier material.

11. The method according to claim 10, wherein said carrier comprises an aqueous solution containing at least one sugar.

12. The method according to claim 11, wherein said sugar comprises at least one member of the group consisting of fructose, sucrose, and mixtures thereof, and optionally glucose.

13. The method according to claim 11, wherein said aqueous solution contains a ratio of ~D-glucose: 2 D-fructose: sucrose.

14. The method according to claim 1, wherein said *Anastrepha* species is *Anastrepha suspensa*.

15. The method according to claim 14, wherein said *Anastrepha suspensa* are males.

16. The method according to claim 14, wherein said *Anastrepha suspensa* are females.

17. The method according to claim 14, wherein said *Anastrepha suspensa* are *Anastrepha suspensa* males and *Anastrepha suspensa* females.

18. A composition comprising suspensolide and at least one member of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a carrier or carrier material; said composition containing no β-bisabolene and no α-farnesene.

19. The composition according to claim 18, wherein said composition contains no (Z)-3-nonen-1-ol, no (Z,Z)-3,6-nanadien-1-ol, and no (Z)-β-ocimene.

20. The composition according to claim 18, wherein said composition comprises suspensolide and at least two members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof.

21. The composition according to claim 18, wherein said composition comprises suspensolide and at least three members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof.

22. The composition according to claim 18, wherein said composition comprises suspensolide, γ-hydroxy acid of epianastrephin, γ-hydroxy acid of anastrephin, 2,6-dimethyl-6- vinyl-cyclohexeneacetic acid, and β-D-glucopyranosyl 2,6-dimethyl-6-vinyl-cyclohex-1-ene-1-acetoate.

23. The composition according to claim 18, wherein said composition contains 2,6-dimethyl-6-vinyl-cyclohexeneacetic acid.

24. The composition according to claim 18, wherein said composition contains β-D-glucopyranosyl 2,6-dimethyl-6-vinyl-cyclohex-1-ene-1-acetoate.

25. The composition according to claim 18, wherein said composition contains 2,6-dimethyl-6-vinyl-cyclohexeneacetic acid and β-D-glucopyranosyl 2,6-dimethyl-6-vinyl-cyclohex-1-ene-1-acetoate.

26. The composition according to claim 18, wherein said composition consists of suspensolide and at least one member of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a control agent for insects.

27. The method according to claim 1, wherein said composition comprises suspensolide and at least two members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof.

28. The method according to claim 1, wherein said composition comprises suspensolide and at least three members of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof.

29. The method according to claim 1, wherein said composition comprises suspensolide, γ-hydroxy acid of epianastrephin, γ-hydroxy acid of anastrephin, 2,6-dimethyl-6-vinyl-cyclohexeneacetic acid, and β-D-glucopyranosyl 2,6-dimethyl-6-vinyl-cyclohex-1-ene-1-acetoate.

30. The method according to claim 1, wherein said composition contains 2,6-dimethyl-6-vinyl-cyclohexeneacetic acid.

31. The method according to claim 1, wherein said composition contains β-D-glucopyranosyl 2,6-dimethyl-6-vinyl-cyclohex-1-ene-1-acetoate.

32. The method according to claim 1, wherein said composition contains 2,6-dimethyl-6-vinyl-cyclohexeneacetic acid and β-D-glucopyranosyl 2,6-dimethyl-6-vinyl-cyclohex-1-ene-1-acetoate.

33. The method according to claim 1, wherein said composition consists of suspensolide and at least one member of the group consisting of γ-hydroxy acid of epianastrephin, γ-hydroxy acid of anastrephin, 2,6-dimethyl-6-vinyl-cyclohexeneacetic acid, β-D-glucopyranosyl 2,6-dimethyl-6-vinyl-cyclohex-1-ene-1-acetoate, and mixtures thereof, and optionally a control agent for insects.

* * * * *